United States Patent
Yamaya

(10) Patent No.: US 11,337,599 B2
(45) Date of Patent: May 24, 2022

(54) WASHING TOOL AND ENDOSCOPE SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 178 days.

(21) Appl. No.: 16/253,389

(22) Filed: Jan. 22, 2019

(65) Prior Publication Data

US 2019/0150722 A1    May 23, 2019

Related U.S. Application Data

(63) Continuation of application No. PCT/JP2017/024689, filed on Jul. 5, 2017.

(30) Foreign Application Priority Data

Aug. 26, 2016    (JP) .............................. JP2016-166069

(51) Int. Cl.
*A61B 1/12* (2006.01)
*G02B 23/24* (2006.01)
(Continued)

(52) U.S. Cl.
CPC ................ *A61B 1/125* (2013.01); *A61B 1/12* (2013.01); *B08B 3/10* (2013.01); *G02B 23/24* (2013.01);
(Continued)

(58) Field of Classification Search
CPC .... A61B 1/125; G02B 23/24; G02B 23/2476; G02B 27/0006; B08B 3/10
See application file for complete search history.

(56) References Cited

U.S. PATENT DOCUMENTS

| | | | |
|---|---|---|---|
| 5,090,433 A | * | 2/1992 | Kamaga ................. A61B 1/122 134/169 C |
| 6,919,057 B2 | * | 7/2005 | Halstead .................. A61L 2/28 422/297 |

(Continued)

FOREIGN PATENT DOCUMENTS

| | | |
|---|---|---|
| JP | H08-252211 A | 10/1996 |
| JP | 2015181914 A * | 10/2015 |

(Continued)

OTHER PUBLICATIONS

Machine English translation of Description of WO 2015/107801 A1 (Onishi, Jul. 2015) (Year: 2015).*

(Continued)

*Primary Examiner* — Joseph L. Perrin
*Assistant Examiner* — Irina Graf
(74) *Attorney, Agent, or Firm* — Scully, Scott, Murphy & Presser, P.C.

(57) ABSTRACT

A washing tool includes a washing tool main body and a supplier. The washing tool main body is attached to a distal framing section of an insertion section of an endoscope in place of a cover, the cover being configured to be attached to the distal framing section. The washing tool main body accommodates the distal framing section in an inside of the washing tool main body in a state where the washing tool main body is attached to the distal framing section. The supplier is configured to supply a fluid to the inside of the washing tool main body.

4 Claims, 24 Drawing Sheets

(51) Int. Cl.
    *B08B 3/10*    (2006.01)
    *G02B 27/00*    (2006.01)

(52) U.S. Cl.
    CPC ..... *G02B 23/2476* (2013.01); *G02B 27/0006* (2013.01)

(56) References Cited

U.S. PATENT DOCUMENTS

| | | | | |
|---|---|---|---|---|
| 2004/0118440 | A1* | 6/2004 | Sasaki | A61B 90/70 134/166 C |
| 2006/0020165 | A1* | 1/2006 | Adams | A61B 1/00094 600/121 |
| 2008/0188715 | A1* | 8/2008 | Fujimoto | G02B 27/0006 600/157 |
| 2014/0318582 | A1* | 10/2014 | Mowlai-Ashtiani | A61B 90/70 134/22.11 |
| 2015/0087907 | A1* | 3/2015 | Konstorum | A61B 1/126 600/121 |
| 2015/0173597 | A1* | 6/2015 | Sato | A61B 1/00128 134/166 C |
| 2015/0190041 | A1* | 7/2015 | Suehara | A61B 1/126 600/109 |
| 2016/0193012 | A1* | 7/2016 | Anderson | A61B 90/361 606/130 |
| 2018/0147022 | A1* | 5/2018 | Gupta | A61B 1/122 |

FOREIGN PATENT DOCUMENTS

| | | | | |
|---|---|---|---|---|
| WO | 2015/107801 | A1 | 7/2015 | |
| WO | 2016/059921 | A1 | 4/2016 | |
| WO | WO-2016059383 | A2 * | 4/2016 | ......... A61B 1/00059 |

OTHER PUBLICATIONS

International Search Report dated Sep. 26, 2017 issued in International Application No. PCT/JP2017/024689.
English translation of International Preliminary Report on Patentability dated Mar. 7, 2019, together with the Written Opinion received in related International Application No. PCT/JP2017/024689.
Chinese Office Action dated Mar. 3, 2021 received in 201780050210.3.

* cited by examiner

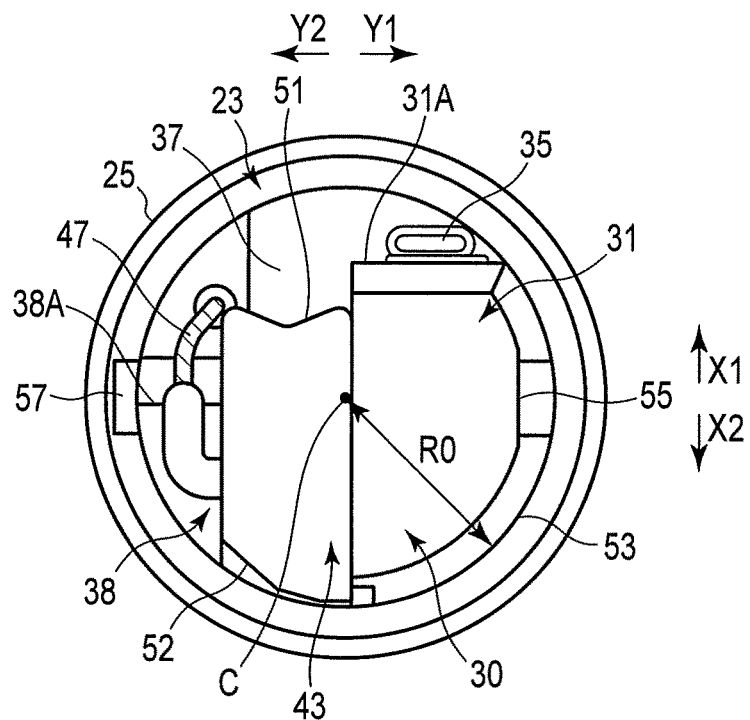
F I G. 3D
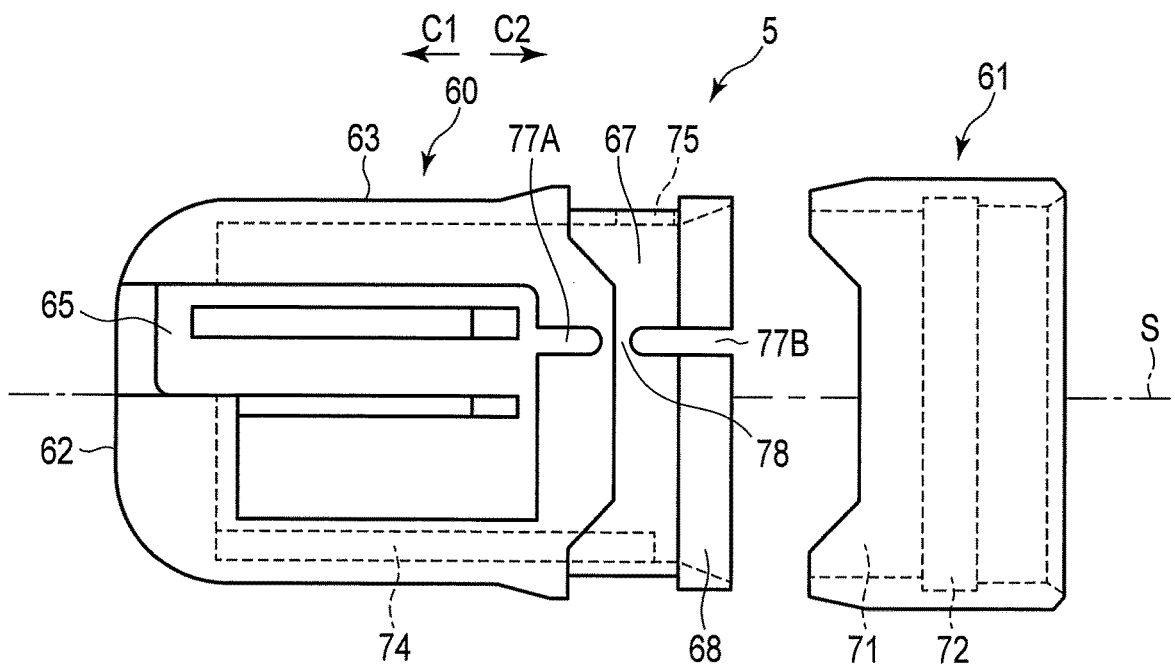
F I G. 4A

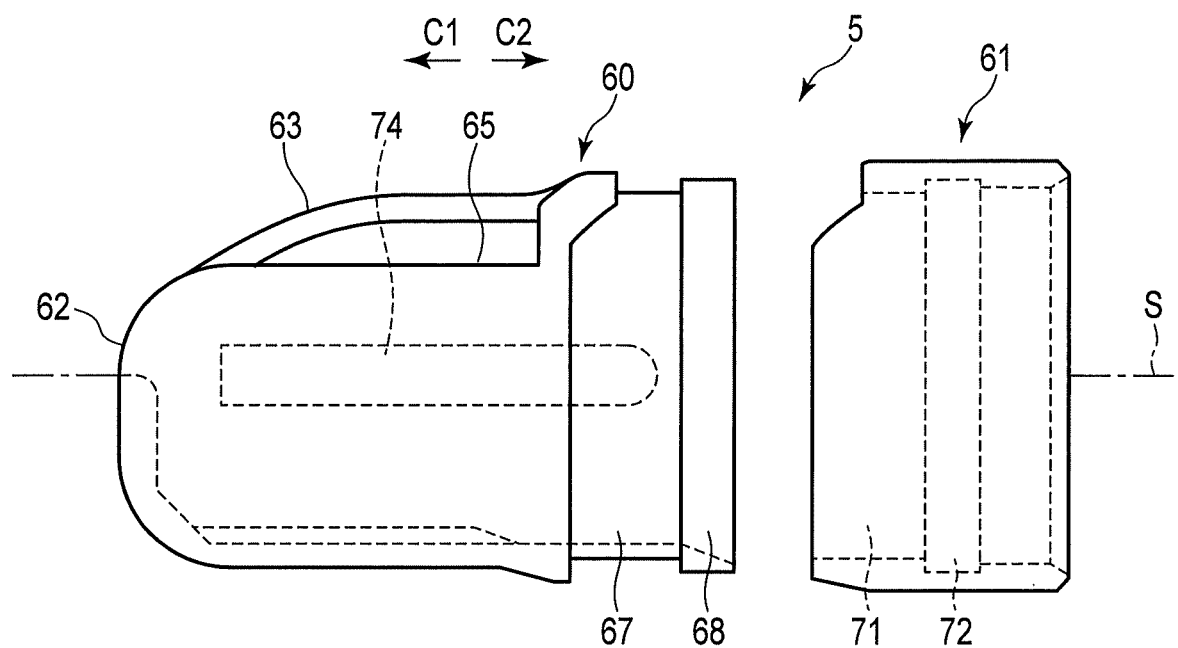
F I G. 4B
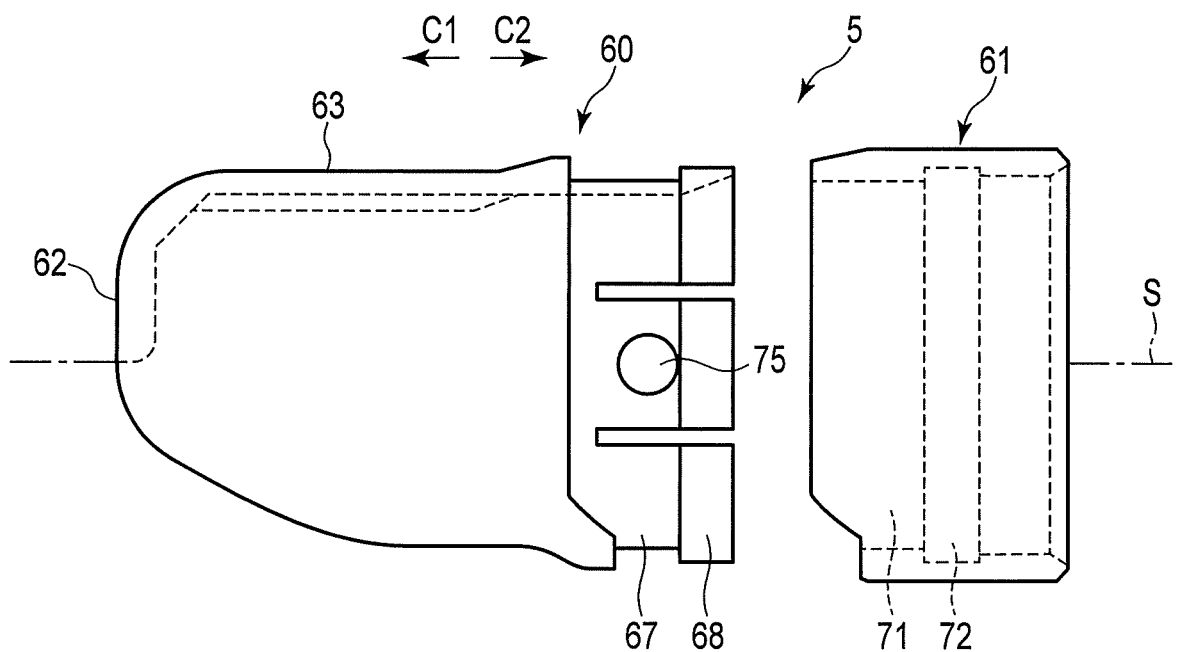
F I G. 4C

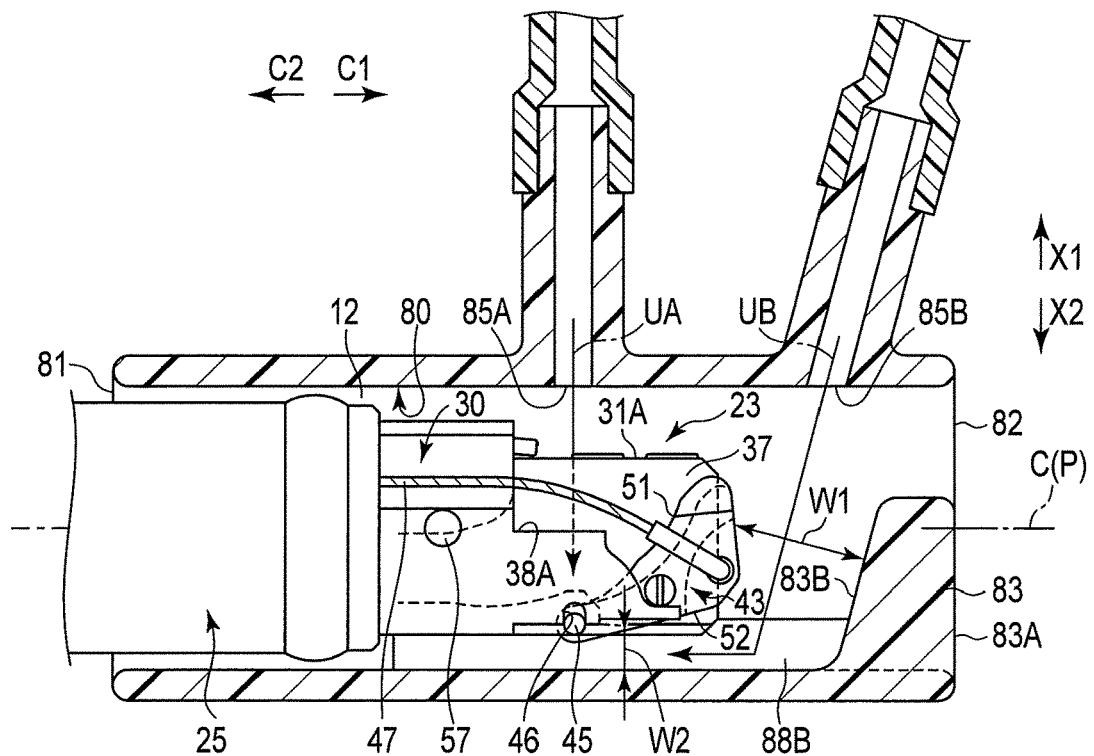
F I G. 8
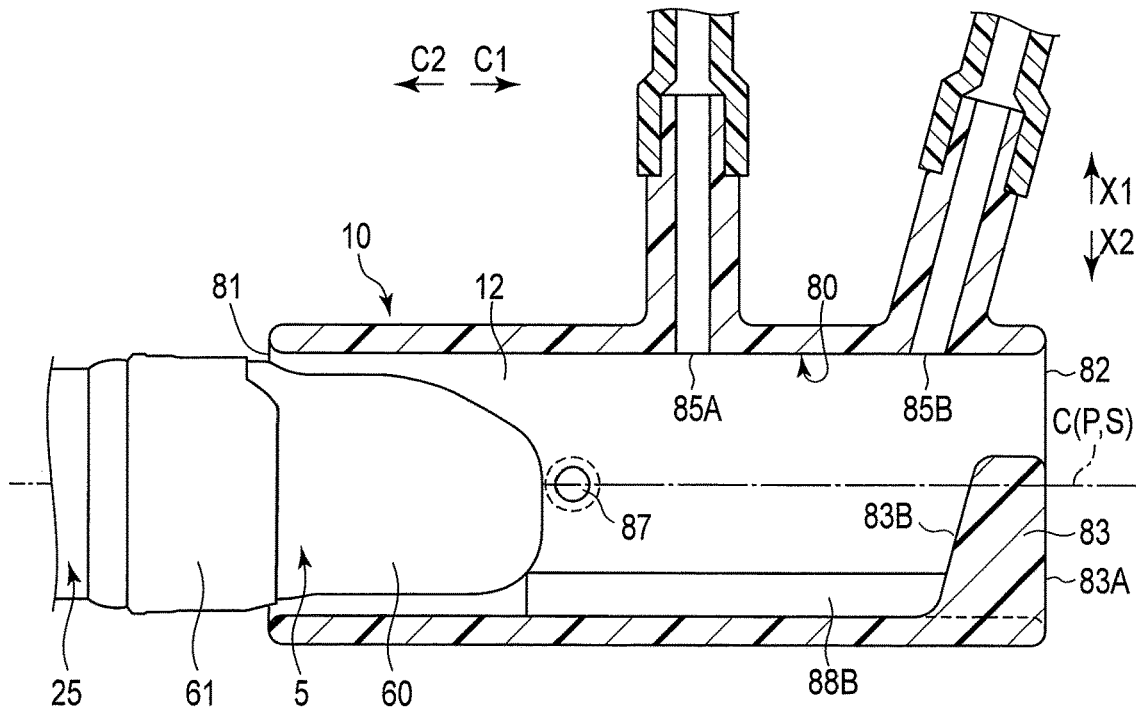
F I G. 9A

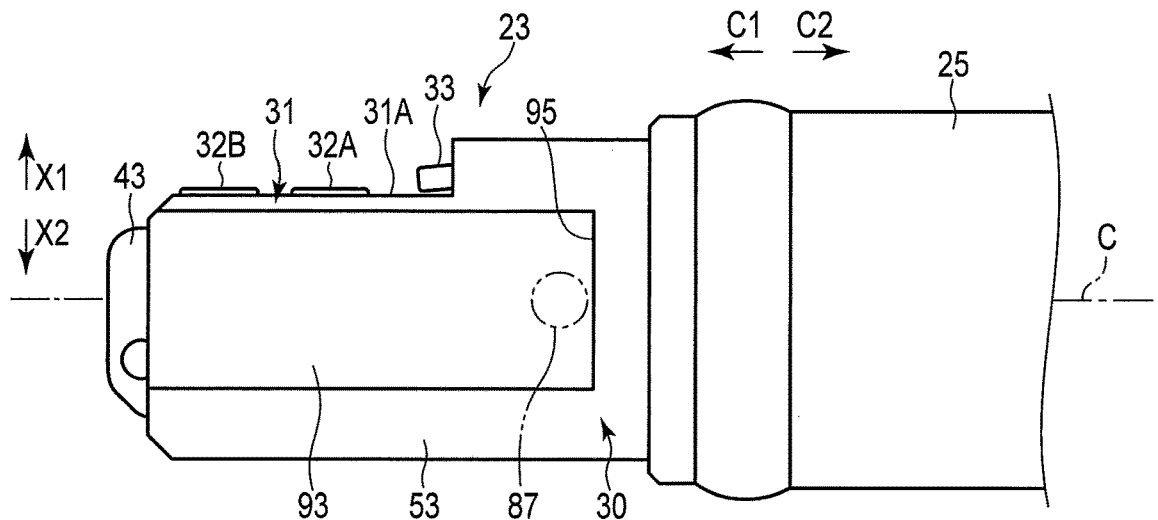
F I G. 10A
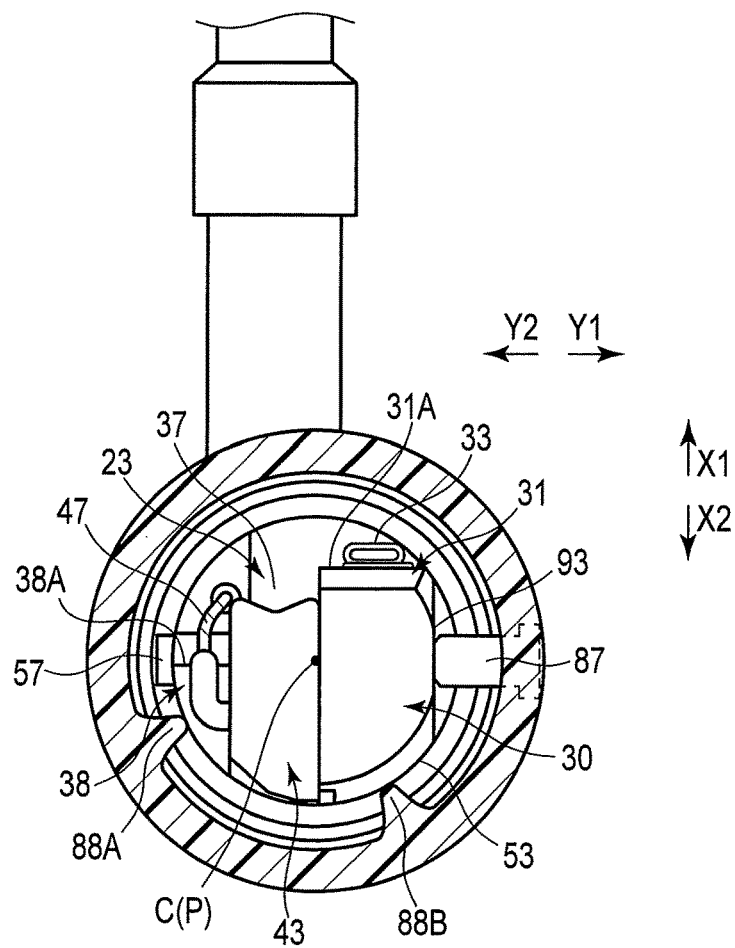
F I G. 10B

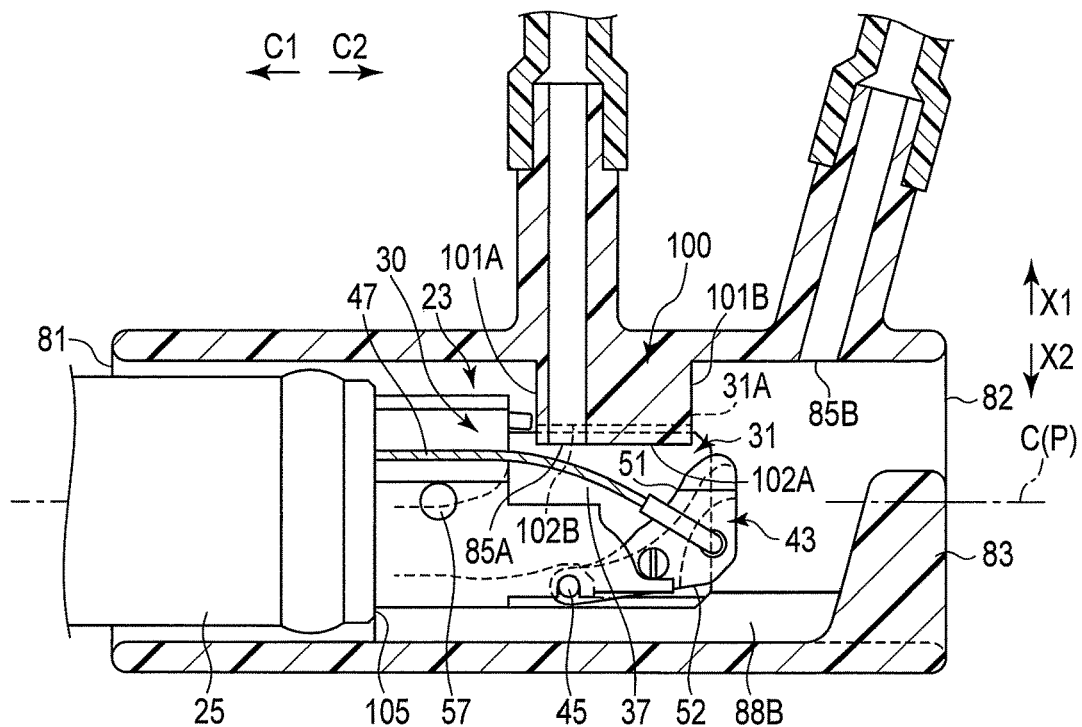
F I G. 12A
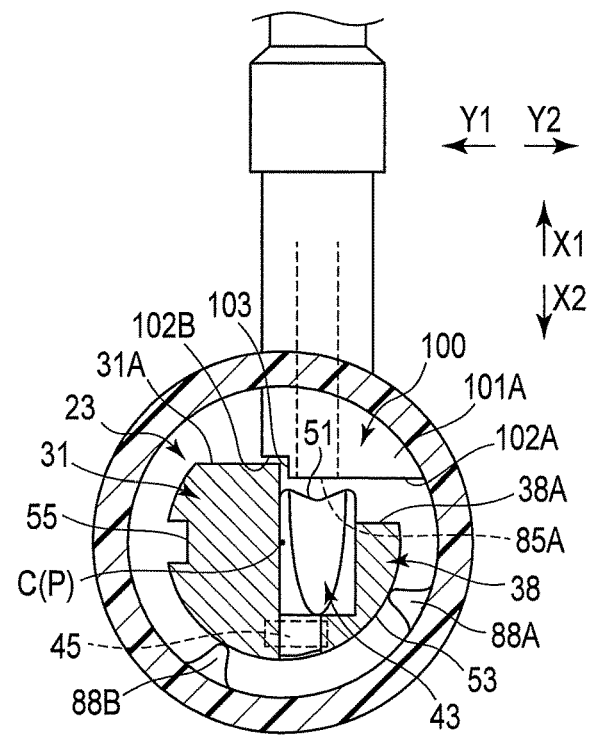
F I G. 12B

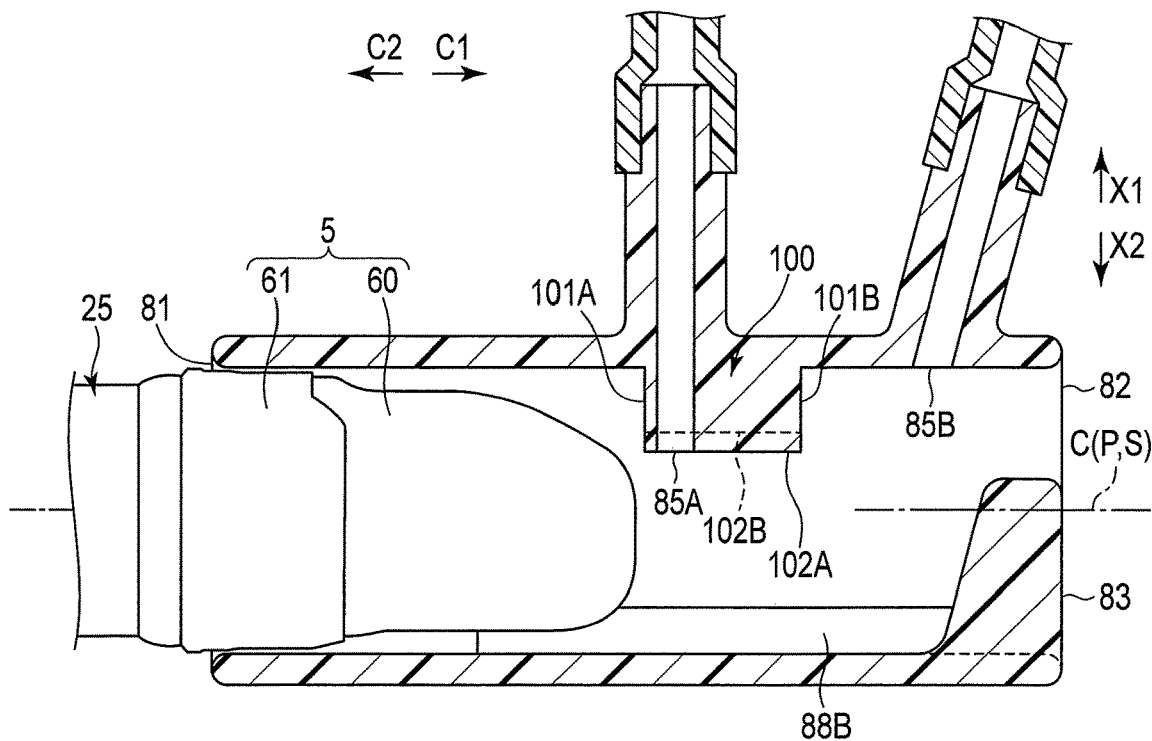
F I G. 13A
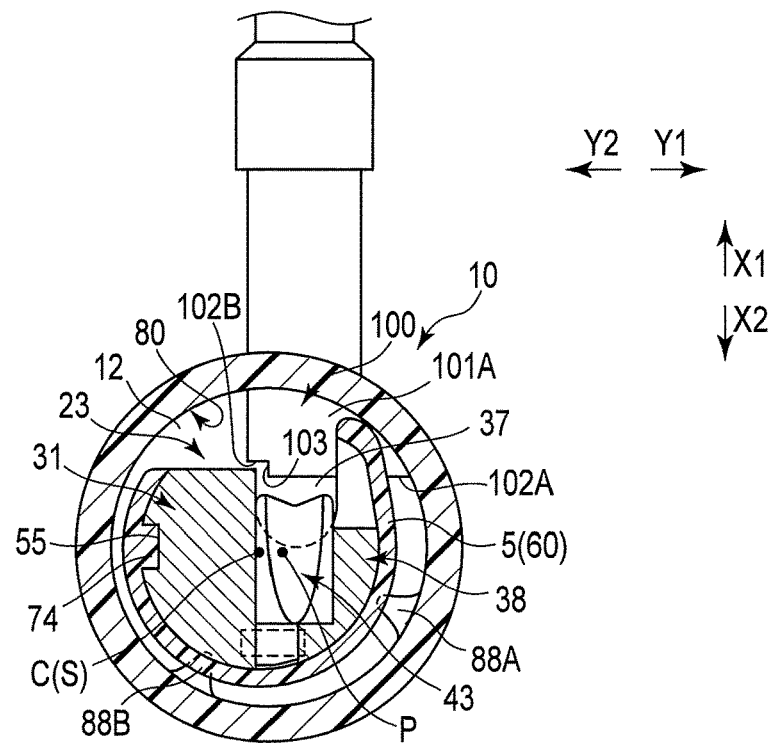
F I G. 13B

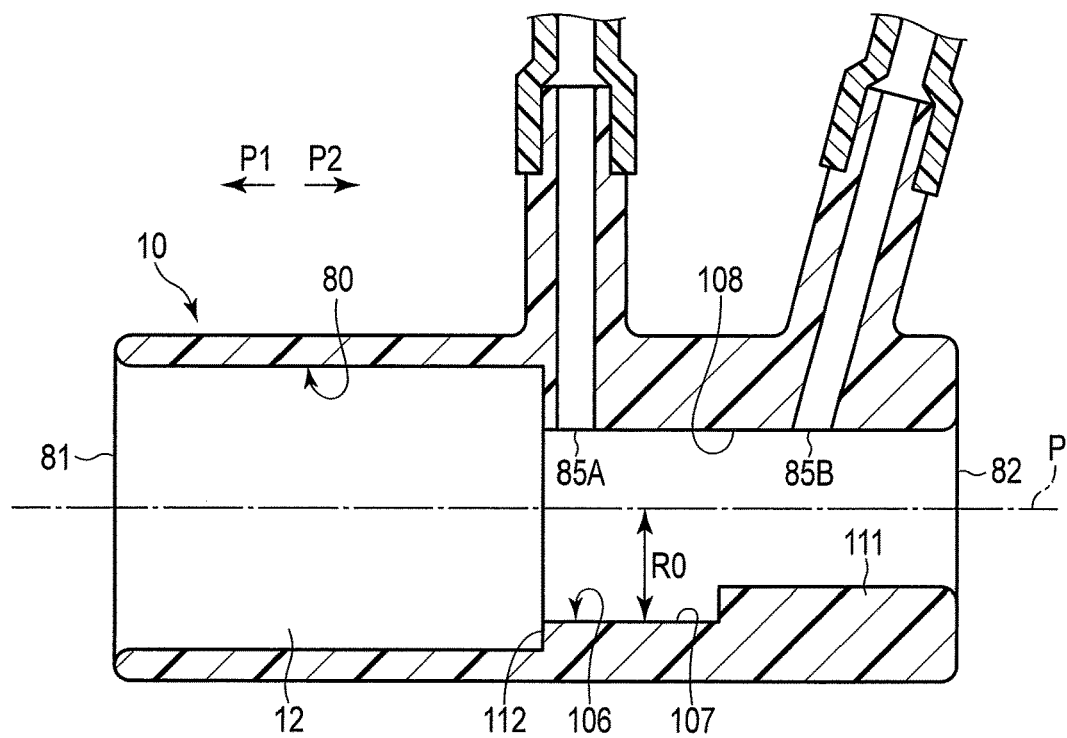
F I G. 14A
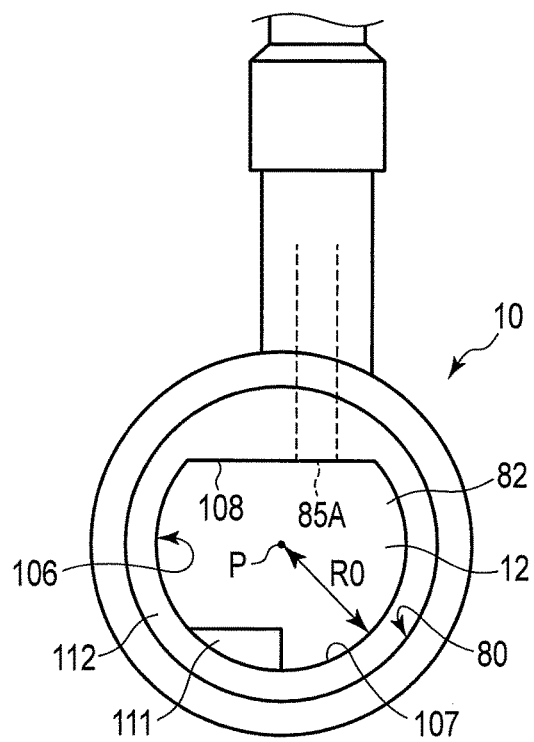
F I G. 14B

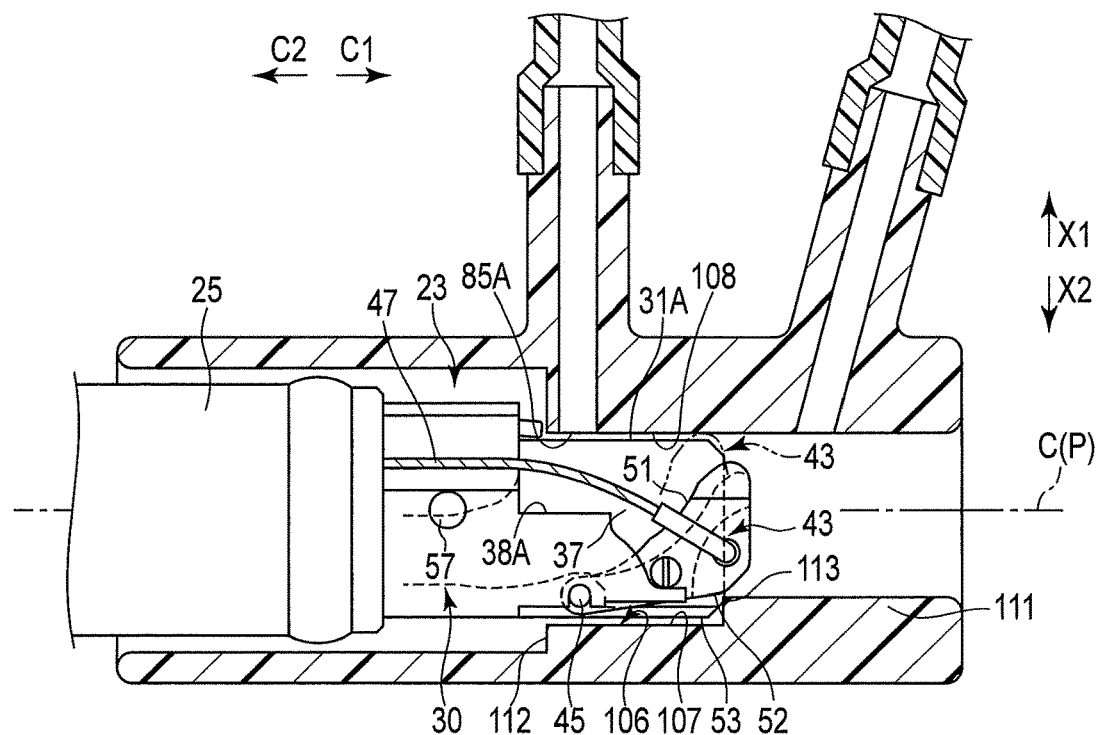
F I G. 15A
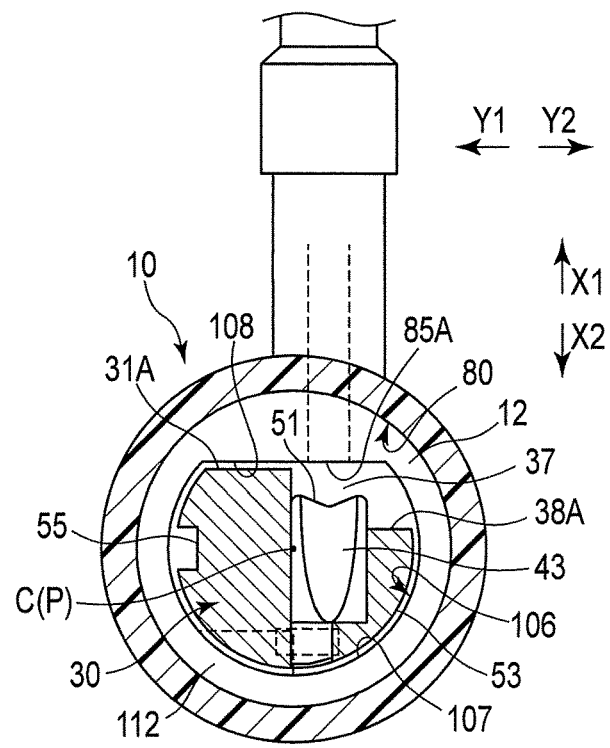
F I G. 15B

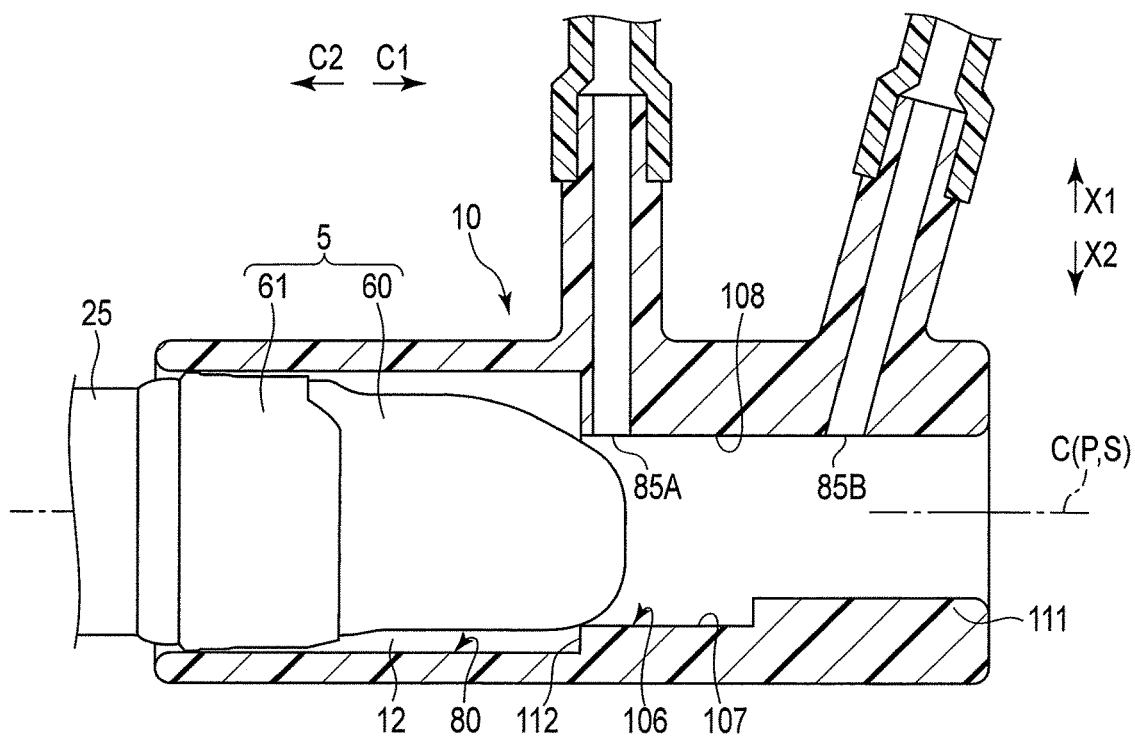
F I G. 16A
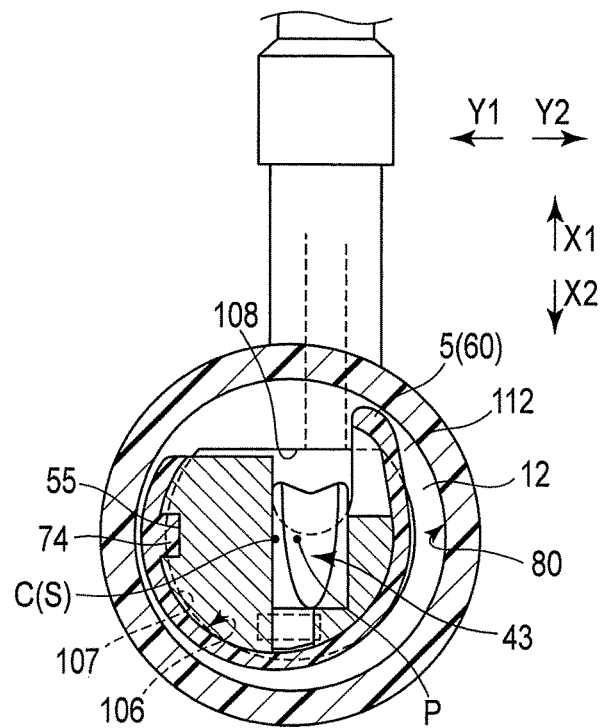
F I G. 16B

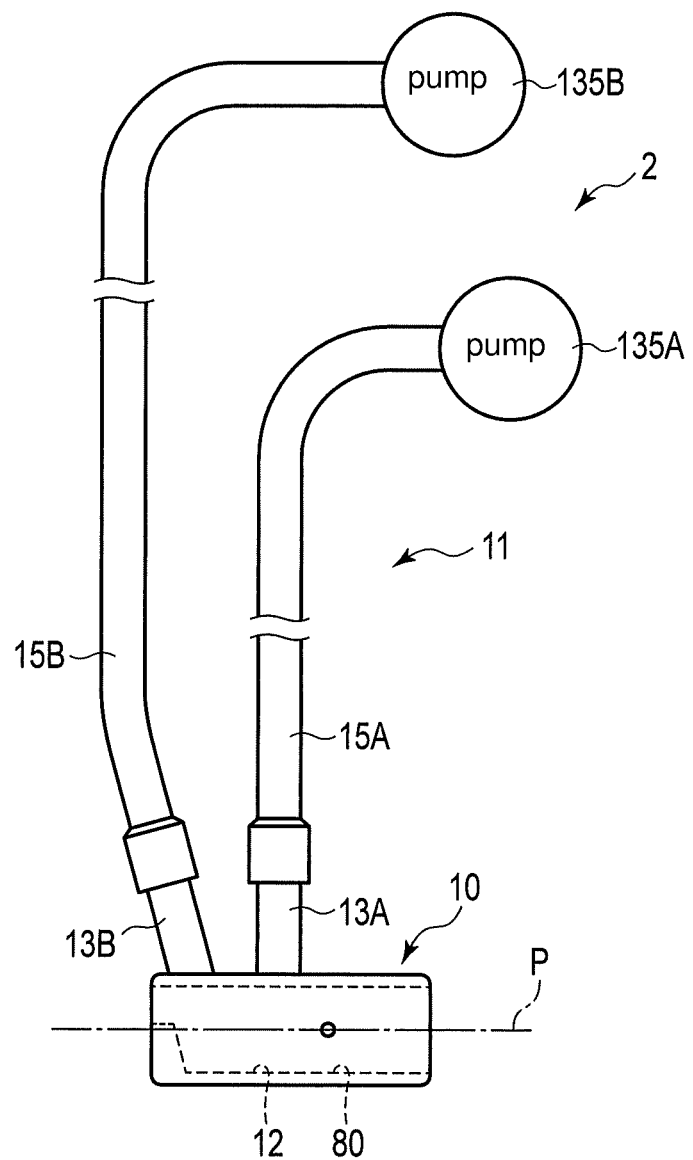
F I G. 21

WASHING TOOL AND ENDOSCOPE SYSTEM

CROSS-REFERENCE TO RELATED APPLICATIONS

This is a Continuation Application of PCT Application No. PCT/JP2017/024689, filed Jul. 5, 2017 and based upon and claiming the benefit of priority from prior Japanese Patent Application No. 2016-166069, filed Aug. 26, 2016, the entire contents of which are incorporated herein by reference.

BACKGROUND OF THE INVENTION

1. Field of the Invention

The present invention relates to a washing tool for washing a distal framing section of an insertion section of an endoscope, and relates to an endoscope system including the washing tool and the endoscope.

2. Description of the Related Art

Jpn. Pat. Appln. KOKAI Publication No. H8-252211 discloses a structure in which a cover is detachably attached to a distal framing section of an insertion section of an endoscope. When washing the distal framing section of the endoscope, a cup is filled with a liquid such as a washing liquid and water. Then, the cover is detached from the distal framing section, so that the distal framing section is washed while being immersed in the liquid filled in the cup.

BRIEF SUMMARY OF THE INVENTION

According to one aspect of the invention, a washing tool includes that: a washing tool main body configured to be attached to a distal framing section of an insertion section of an endoscope in place of a cover which is configured to be attached to the distal framing section, the washing tool main body being configured to accommodate the distal framing section in an inside of the washing tool main body in a state where the washing tool main body is attached to the distal framing section; and a supplier configured to supply a fluid to the inside of the washing tool main body.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3D is a schematic diagram of the distal framing section of the first embodiment viewed from a distal side, FIG. 4A is a schematic diagram of the cover to be attached to the distal framing section of the first embodiment viewed from a side where an opening hole is open to the outside, FIG. 4B is a schematic diagram of the cover of the first embodiment viewed from a side where a guide protrusion is located with respect to a central axis, FIG. 4C is a schematic diagram of the cover of the first embodiment viewed from a side where a lock hole is located with respect to the central axis, FIG. 8 is a cross-sectional diagram schematically showing a state in which a washing liquid is being supplied to the distal framing section located at a predetermined position in a storage portion of the washing tool main body of the first embodiment, as viewed in a cross section substantially perpendicular to the second intersecting direction, FIG. 9A is a cross-sectional diagram schematically showing a state in which the distal framing section with the cover of the first embodiment attached thereto is inserted in the storage portion of the washing tool main body, as viewed in a cross section substantially perpendicular to the second intersecting direction, FIG. 10A is a schematic diagram of a distal framing section of a first modification viewed from one side in the second intersecting direction, FIG. 10B is a cross-sectional diagram schematically showing a state in which a washing tool main body of the first modification is attached to the distal framing section, as viewed in a cross section substantially perpendicular to the longitudinal axis and passing through a position located on an opening window side with respect to a distal end of the distal framing section, FIG. 12A is a cross-sectional diagram schematically showing a state in which the washing tool main body is attached to a distal framing section of the second modification, as viewed in a cross section substantially perpendicular to the second intersecting direction, FIG. 12B is a cross-sectional diagram schematically showing a state in which the washing tool main body is attached to the distal framing section of the second modification, as viewed in a cross section substantially perpendicular to the longitudinal axis and passing through the distal framing section, FIG. 13A is a cross-sectional diagram schematically showing a state in which the distal framing section with a cover of the second modification attached thereto is inserted in the storage portion of the washing tool main body, as viewed in a cross section substantially perpendicular to the second intersecting direction, FIG. 13B is a cross-sectional diagram schematically showing a state in which the distal framing section with the cover of the second modification attached thereto is inserted in the storage portion of the washing tool main body, as viewed in a cross section substantially perpendicular to the longitudinal axis and passing through the distal framing section and the cover, FIG. 14A is a cross-sectional diagram schematically showing a washing tool main body of a third modification, as viewed in a cross section substantially parallel with the central axis and passing through connection sleeves, FIG. 14B is a schematic diagram of the washing tool main body of the third modification viewed from the insertion opening side, FIG. 15A is a cross-sectional diagram schematically showing a state in which the washing tool main body is attached to a distal framing section of the third modification, as viewed in a cross section substantially perpendicular to the second intersecting direction, FIG. 15B is a cross-sectional diagram schematically showing a state in which the washing tool main body is attached to the distal framing section of the third modification, as viewed in a cross section substantially perpendicular to the longitudinal axis and passing through the distal framing section, FIG. 16A is a cross-sectional diagram schematically showing a state in which the distal framing section with a cover of the third modification attached thereto is inserted in the storage portion of the washing tool main body, as viewed in a cross section substantially perpendicular to the second intersecting direction, FIG. 16B is a cross-sectional diagram schematically showing a state in which the distal framing section with the cover of the third modification attached thereto is inserted in the storage portion of the washing tool main body, as viewed in a cross section substantially perpendicular to the longitudinal axis and passing through the distal framing section and the cover, FIG. 21 is a schematic diagram of a washing tool of a seventh modification.

DETAILED DESCRIPTION OF THE INVENTION

First Embodiment

A first embodiment of the present invention will be described with reference to FIGS. 1 to 9B.

Figure 1:
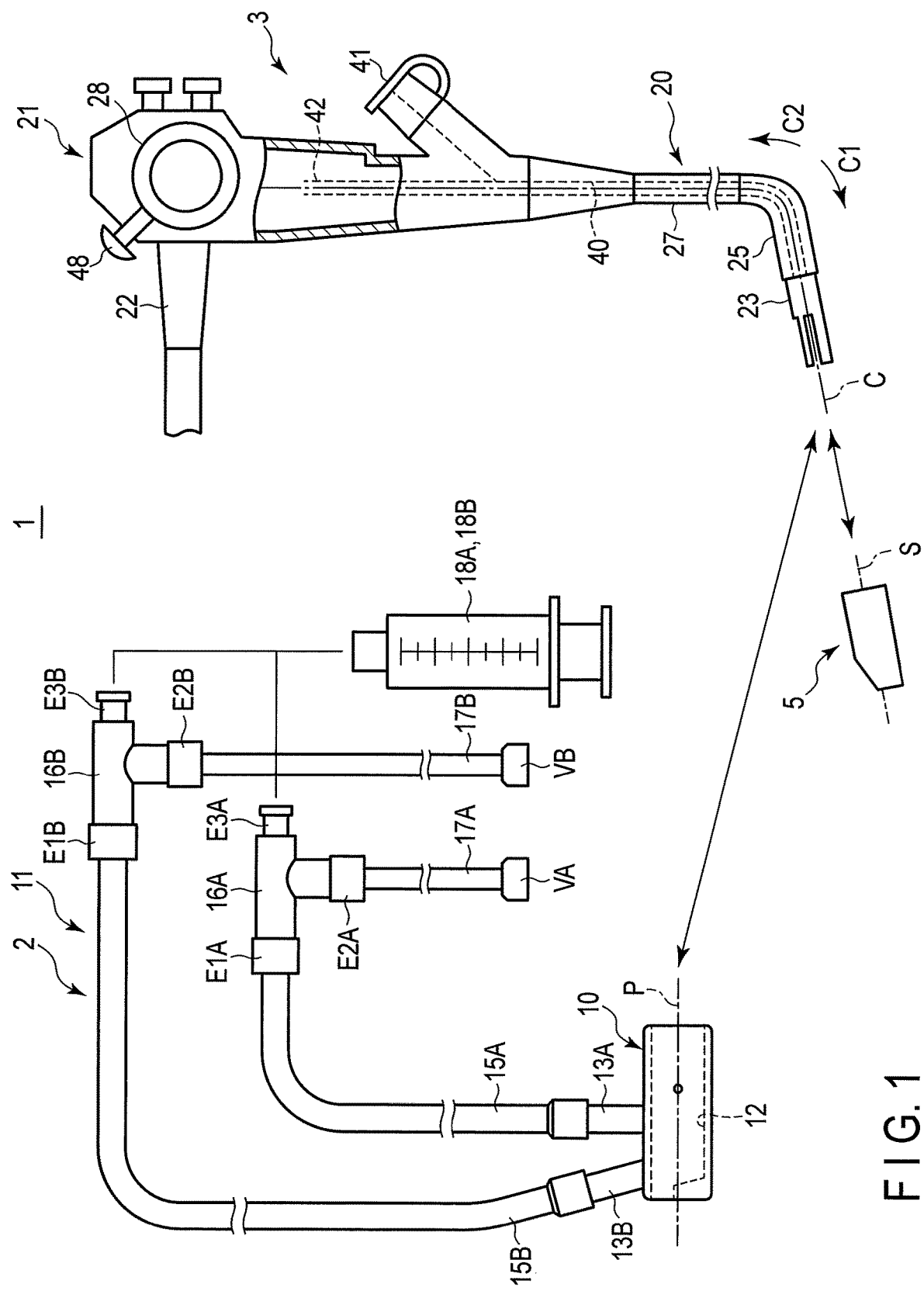
FIG. 1 is a schematic diagram of an endoscope system of a first embodiment.

FIG. 1 shows an endoscope system 1 of the present embodiment. The endoscope system 1 includes a washing tool 2, as shown in FIG. 1. The washing tool 2 includes a washing tool main body 10 and a supply section (supplier) 11. A storage portion (storage cavity) 12, which is a cavity for accommodating a washing target, is formed inside the washing tool main body 10, so that the washing tool main body 10 has a hollow shape. The supply section 11 supplies a fluid such as a washing liquid to the storage portion 12 in the washing tool main body 10. Examples of a material forming the washing tool main body 10 include, but are not limited to, polycarbonate, a modified PPE resin, polysulfone containing glass, polyphenylsulfone, and stainless steel.

Connection sleeves 13A and 13B are provided on an outer peripheral portion of the washing tool main body 10. The supply section 11 includes supply tubes 15A and 15B, branch pipes 16A and 16B, suction tubes 17A and 17B, and syringes 18A and 18B. The branch pipe 16A includes an outflow end E1A, an inflow end E2A, and a syringe connection end E3A. The branch pipe 16B includes an outflow end E1B, an inflow end E2B, and a syringe connection end E3B. One end of the supply tube 15A is connected to the connection sleeve 13A, and the other end of the supply tube 15A is connected to the outflow end E1A of the branch pipe 16A. Likewise, one end of the supply tube 15B is connected to the connection sleeve 13B, and the other end of the supply tube 15B is connected to the outflow end E1B of the branch pipe 16B. One end of the suction tube 17A is connected to the inflow end E2A of the branch pipe 16A, and one end of the suction tube 17B is connected to the inflow end E2B of the branch pipe 16B. A suction port VA is formed at the other end of the suction tube 17A, and a suction port VB is formed at the other end of the suction tube 17B. The syringe 18A is attached to the syringe connection end E3A of the branch pipe 16A, and the syringe 18B is attached to the syringe connection end E3B of the branch pipe 16B.

When the syringe 18A is actuated while the suction port VA is immersed in a liquid such as a washing liquid, the liquid as a fluid flows from the suction port VA into the storage portion 12 of the washing tool main body 10 through the suction tube 17A, the branch pipe 16A, and the supply tube 15A in the mentioned order. Likewise, when the syringe 18B is actuated while the suction port VB is immersed in a liquid such as a washing liquid, the liquid as a fluid flows from the suction port VB into the storage portion 12 of the washing tool main body 10 through the suction tube 17B, the branch pipe 16B, and the supply tube 15B in the mentioned order. As a result, the fluid such as a washing liquid is supplied to the storage portion 12.

The endoscope system 1 includes an endoscope 3, which is an insertion device. The endoscope 3 includes an elongated insertion section 20 to be inserted into a conduit such as a lumen. The insertion section 20 extends along a longitudinal axis C defined as a central axis. One side along the longitudinal axis C is defined as a distal side (arrow C1 side), and a side opposite to the distal side is defined as a proximal side (arrow C2 side). The endoscope 3 includes an operation section 21 provided on the proximal side with respect to the insertion section 20. A proximal end of the insertion section 20 is connected to the operation section 21, and the operation section 21 can be held by a user. One end of a universal cord 22 is connected to the operation section 21. The endoscope 3 is used together with one or more of peripheral devices (not shown in the drawings). The other end of the universal cord 22 is connected to one of peripheral devices. Examples of the peripheral devices include an image processing device (image processor), a display device (display), a light source device (light source), an air supply source device (air supply source), a liquid supply source device (liquid supply source), and a suction source device (suction source).

The insertion section 20 includes a distal framing section (distal frame) 23, a bending section (bending tube) 25 connected to the proximal side of the distal framing section 23, and a tubular section (elongated tube) 27 connected to the proximal side of the bending section 25. The distal framing section 23 is provided in a distal portion of the insertion section 20, and forms a distal end of the insertion section 20. In one example, the tubular section 27 has flexibility, so that the endoscope 3 is a so-called flexible endoscope. In other example, the tubular section 27 is rigid, so that the endoscope 3 is a so-called rigid endoscope. The bending section 25 is bent by, for example, operating a knob 28 of the operation section 21. In this case, the known bending mechanism is actuated based on the operation of the knob 28, whereby the bending section 25 is bent. Also, in one example, a distal end of the tubular section 27 may be connected to the distal framing section 23 without providing the bending section 25.

The endoscope system 1 includes a cover 5. The cover 5 is detachably attached to the distal framing section 23. While using the endoscope 3, for example, observing a lumen using the endoscope 3, the cover 5 is attached to the distal framing section 23. In one example, the cover 5 is replaced each time the endoscope 3 is used. In this case, the cover 5 is detached from the distal framing section 23 by, for example, destroying a part of the cover 5 using a predetermined jig or by hand after using the endoscope 3. Then, the detached cover 5 is discarded. In other example, after using the endoscope 3, the cover 5 is detached from the distal framing section 23 without destroying the cover 5, and the detached cover 5 is washed and sterilized. Then, before using the endoscope 3 next time, the cover 5 is reattached to the distal framing section 23, so that the cover 5 is reused. In either case, the cover 5 attached to the distal framing section 23 is not easily detached from the distal framing section 23 when the endoscope 3 is used.

The washing tool main body 10 is attached to the distal framing section 23 in a state where the cover 5 is detached from the distal framing section 23. Namely, the washing tool main body 10 is attached to the distal framing section 23 instead of the cover 5. With the washing tool main body 10 attached to the distal framing section 23, the distal framing section 23 is housed in the storage portion 12 inside the washing tool main body 10.

Figure 2:
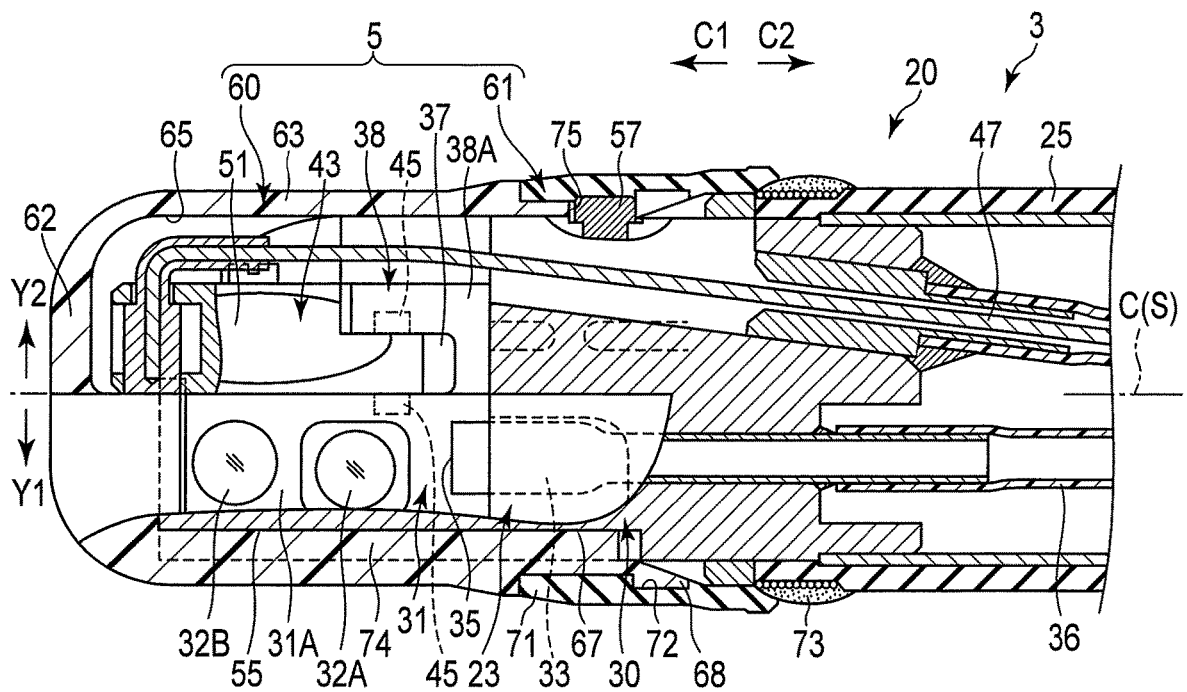
FIG. 2 is a cross-sectional diagram schematically showing a state in which a cover is attached to a distal framing section of the first embodiment, as viewed in a cross section substantially perpendicular to a first intersecting direction.
Figure 3A:
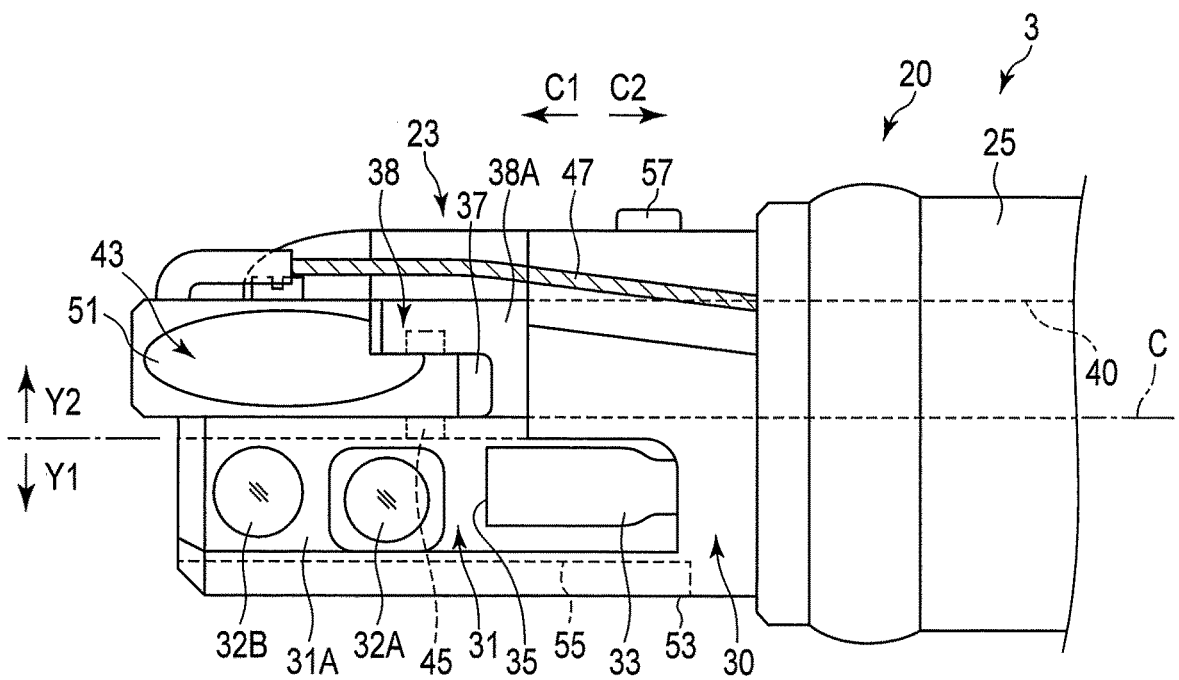
FIG. 3A is a schematic diagram of the distal framing section of the first embodiment viewed from one side in the first intersecting direction.
Figure 3B:
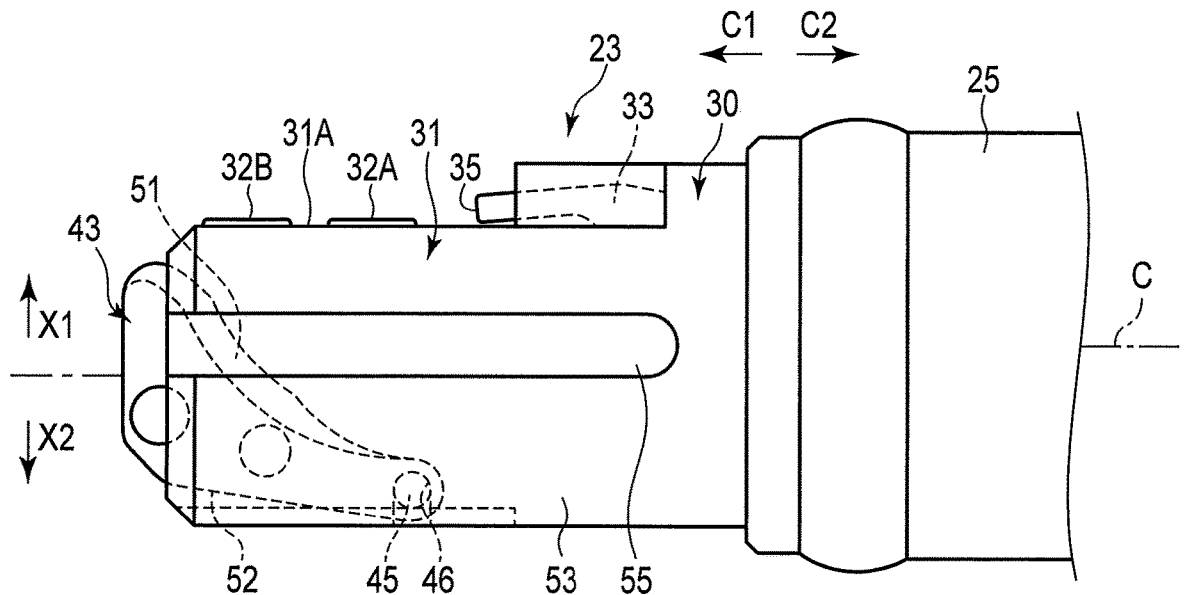
FIG. 3B is a schematic diagram of the distal framing section of the first embodiment viewed from one side in a second intersecting direction.
Figure 3C:
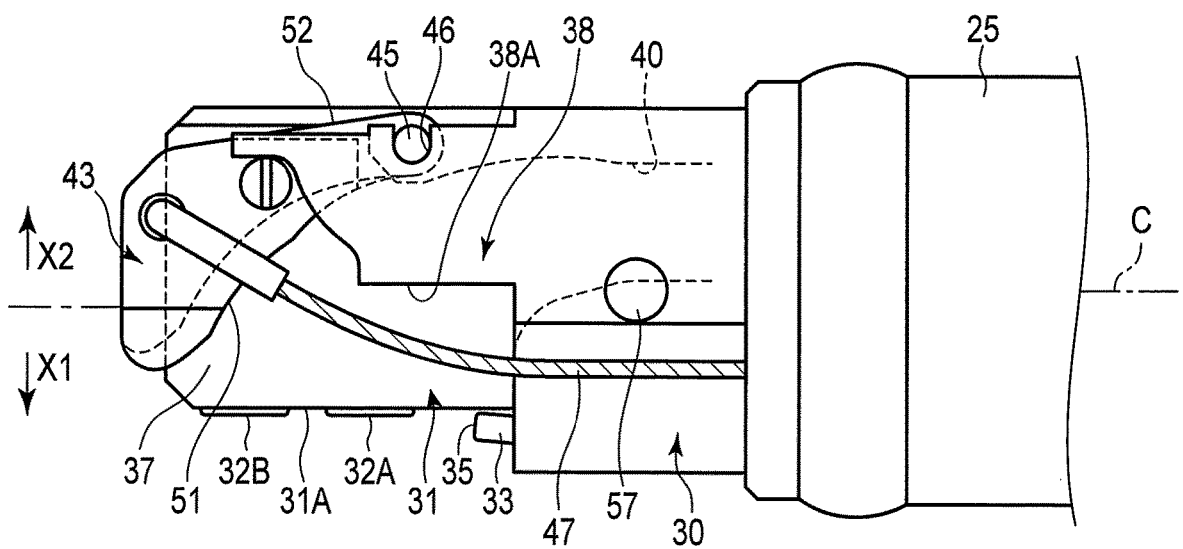
FIG. 3C is a schematic diagram of the distal framing section of the first embodiment viewed from the other side in the second intersecting direction.

FIG. 2 shows a state in which the cover 5 is attached to the distal framing section 23. FIGS. 3A to 3D show the distal framing section 23 in a state where neither the cover 5 nor the washing tool main body 10 is attached to the distal framing section 23. A first intersecting direction (direction indicated by arrows X1 and X2) intersecting the longitudinal axis C is defined, and a second intersecting direction (direction indicated by arrows Y1 and Y2) intersecting the longitudinal axis C and intersecting the first intersecting direction is defined. FIG. 2 shows a cross section substantially perpendicular to the first intersecting direction, and FIG. 3A shows the distal framing section 23 viewed from one side (arrow X1 side) in the first intersecting direction. FIG. 3B shows the distal framing section 23 viewed from one side (arrow Y1 side) in the second intersecting direction, and FIG. 3C shows the distal framing section 23 viewed from the other side (arrow Y2 side) in the second intersecting direction. FIG. 3D shows the distal framing section 23 viewed from the distal side (arrow C1 side). The direction intersecting the longitudinal axis C as the first intersecting direction, and the direction intersecting the longitudinal axis C and the first intersecting direction as the second intersecting direction are each considered to be, for example, a substantially perpendicular direction.

As shown in FIGS. 2 to 3D, the distal framing section 23 includes a block-shaped distal portion main body (distal frame main body) 30. The distal portion main body 30 is formed of a hard material. Examples of the hard material forming the distal portion main body 30 include, but are not limited to, a stainless steel material. The distal portion main body 30 is, for example, connected to the distal side of the bending section 25. The central axis of the distal portion main body 30 is substantially coaxial with the longitudinal axis C. The distal portion main body 30 includes a wall portion (wall) 31, and the wall portion 31 includes a flat surface portion (flat surface) 31A. The flat surface portion 31A forms a part of an outer peripheral surface of the distal portion main body 30 and faces one side (arrow X1 side) in the first intersecting direction. Also, the flat surface portion 31A forms an end face of the wall portion 31 on one side (arrow X1 side) in the first intersecting direction. The wall portion 31 forms an end of the distal portion main body 30 on one side (arrow Y1 side) in the second intersecting direction.

In the flat surface portion 31A, an observation window 32A and an illumination window 32B are fixed to the wall portion 31 of the distal portion main body 30. An imaging element (not shown in the drawings) such as a CCD is built in the distal portion main body 30. The imaging element images an object through the observation window 32A. Then, an image signal is transmitted from the imaging element to the aforementioned image processing device via an imaging cable (not shown in the drawings), the imaging cable extending through the inside of the insertion section 20, the inside of the operation section 21, and the inside of the universal cord 22. As a result, an image of the object is generated by the image processing device, and the generated image is displayed on the aforementioned display device. In the endoscope 3, a light guide (not shown in the drawings) extends through the inside of the insertion section 20, the inside of the operation section 21, and the inside of the universal cord 22. The light emitted from the aforementioned light source device is guided through the light guide. Then, the object is irradiated through the illumination window 32B. In the present embodiment, the illumination window 32B is located on the distal side with respect to the observation window 32A. Also, in the present embodiment, one side (arrow X1 side) in the first intersecting direction is an observing direction of the imaging element. Therefore, the endoscope 3 is formed as a side-viewing or oblique-viewing endoscope in which the direction intersecting the longitudinal axis C of the insertion section 20 is the observing direction of the imaging element. Also, in the present embodiment, the observation window 32A and the illumination window 32B are located on one side (arrow Y1 side) in the second intersecting direction with respect to the longitudinal axis C.

A nozzle 33 is fixed to the distal portion main body 30. In the present embodiment, an ejection port 35 of the nozzle 33 is located on the proximal side and on one side (arrow X1 side) in the first intersecting direction with respect to the observation window 32A and the illumination window 32B. Also, the ejection port 35 is located on a side (arrow Y1 side) where the observation window 32A is located with respect to the longitudinal axis C, according to the second intersecting direction. A distal end of a supply tube 36 is connected to the nozzle 33. A gas such as air is supplied from the aforementioned air supply source device to the nozzle 33 through the supply tube 36. A liquid such as physiological saline is supplied from the aforementioned liquid supply source device to the nozzle 33 through the supply tube 36. The nozzle 33 ejects the supplied liquid and/or gas to the flat surface portion 31A, where the observation window 32A and the illumination window 32B are disposed, from the ejection port 35 toward the distal side.

A cavity 37 is formed in the distal framing section 23 by the distal portion main body 30. The cavity 37 is provided adjacent to the wall portion 31 in the second intersecting direction. The cavity 37 is located on a side (arrow Y2 side) opposite to the observation window 32A in the second intersecting direction with respect to the longitudinal axis C. The cavity 37 opens toward the distal side, one side (arrow X1 side) in the first intersecting direction, and the other side (arrow X2 side) in the first intersecting direction. The distal portion main body 30 includes a wall portion (wall) 38, and the wall portion 38 includes a flat surface portion (flat surface) 38A. The flat surface portion 38A forms a part of the outer peripheral surface of the distal portion main body 30, and faces the observing direction of the imaging element, which is one side (arrow X1 side) in the first intersecting direction. Also, the flat surface portion 38A is located on a side (arrow Y2 side) opposite to the observation window 32A (flat surface portion 31A) in the second intersecting direction with respect to the longitudinal axis C. The wall portion 38 is spaced from the wall portion 31 by the cavity 37 in the second intersecting direction. In the present embodiment, the flat surface portion 38A is located on a side (arrow X2 side) opposite to the observing direction of the imaging element with respect to the flat surface portion 31A, according to the first intersecting direction. The position of the flat surface portion 38A in the first intersecting direction is not limited, and the flat surface portion 38A may located on the same side as the observing direction of the imaging element (arrow X1 side) with respect to the flat surface portion 31A.

A channel 40 extends from the proximal side to the distal side in the insertion section 20, as shown in FIG. 1. The channel 40 extends, for example, through the inside of a channel tube (not shown in the drawings) and the inside of the distal portion main body 30. A distal end of the channel 40 communicates with the cavity 37 in the distal framing section 23. A proximal end of the channel 40 opens to the outside of the endoscope 3 in a distal side portion of the operation section 21. A forceps plug 41 is attached to an opening at the proximal end of the channel 40. Also, a treatment tool (not shown in the drawings) is inserted from the opening at the proximal end of the channel 40 into the channel 40. Then, the treatment tool inserted through the channel 40 protrudes from the cavity 37 of the distal framing section 23 to the outside of the insertion section 20. Namely, the treatment tool protrudes from the cavity 37 to the outside of the insertion section 20 in the state of being inserted through the insertion section 20. Also, a suction path 42 is branched from the channel 40 inside the operation section 21. The suction path 42 extends to the universal cord 22 through a suction changeover valve (not shown in the drawings) of the operation section 21, and opens to the outside of the endoscope 3 at the suction changeover valve. The aforementioned suction source device sucks aspirate from the cavity 37 of the distal framing section 23 through the channel 40 and the suction path 42.

A swing table (raising base) 43 is arranged in the cavity 37 of the distal framing section 23, as shown in FIG. 2 to FIG. 3D. The swing table 43 is arranged between the wall portions 31 and 38 in the cavity 37, according to the second intersecting direction. A support shaft 45 is fixed to the swing table 43. Also, a shaft receiver 46 with which the support shaft 45 is engaged is formed in the distal portion main body 30. The support shaft 45 projects from the swing table 43 to both sides in the second intersecting direction, and the shaft receiver 46 is a groove or a hole into which the portion of the support shaft 45 projecting from the swing table 43 is inserted. The support shaft 45 engages with the shaft receiver 46, whereby the swing table 43 is attached to the distal portion main body 30. The swing table 43 is turnable with respect to the distal portion main body 30 about the central axis of the support shaft 45. Namely, the swing table 43 turns about the central axis of the support shaft 45 as a predetermined rotation axis. In the present embodiment, the central axis of the support shaft 45 is substantially parallel to the second intersecting direction. On the outer peripheral surface of the distal portion main body 30, the shaft receiver 46 opens toward the side (arrow X2 side) opposite to the observing direction of the imaging element. Therefore, the support shaft 45 is exposed to the outside of the insertion section 20 when the cover 5 is not attached to the distal framing section 23. Since the shaft receiver 46 opens, the swing table 43 and the support shaft 45 can be slightly moved on the shaft receiver 46 relative to the distal portion main body 30 in a direction intersecting the central axis of the support shaft 45 when the cover 5 is not attached to the distal framing section 23, so that the swing table 43 and the support shaft 45 rattle against the distal portion main body 30. The slight movement distance of the swing table 43 and the support shaft 45 relative to the distal portion main body 30 is preferably equal to or greater than one fourth of the diameter of the support shaft 45.

A wire 47 extends inside the insertion section 20 from the proximal side toward the distal side. A distal end of the wire 47 is connected to the swing table 43 in the cavity 37 of the distal framing section 23. A proximal end of the wire 47 is connected to a lever 48 (see FIG. 1) provided to the operation section 21. The wire 47 moves toward the proximal side or the distal side based on the manipulation of the lever 48. Thereby, the swing table 43 turns with respect to the distal portion main body 30, as described above, so that the swing table 43 is raised or lowered in the cavity 37.

The swing table 43 includes a first surface 51 facing the observing direction of the imaging element, which is one side (arrow X1 side) in the first intersecting direction, and a second surface 52 facing a side opposite to the first surface 51. The aforementioned treatment tool (not shown in the drawings) inserted through the channel 40 contacts the first surface 51 of the swing table 43 in the cavity 37. Also, the treatment tool protrudes from the cavity 37 to the outside of the insertion section 20 in the observing direction of the imaging element. When the swing table 43 is raised or lowered, the direction of the treatment tool protruding to the outside of the insertion section 20 is changed. As a result, the direction of the treatment tool can be adjusted so that the portion of the treatment tool protruding to the outside of the insertion section 20 is within the visual field of the imaging element.

A curved surface portion (curved surface) 53 is formed on the outer peripheral surface of the distal portion main body 30. The curved surface portion 53 is formed in an arc shape having a radius RO with the longitudinal axis C substantially in the center, when viewed in the cross section substantially perpendicular to the longitudinal axis C. The curved surface portion 53 is continuous between the wall portions 31 and 38. Therefore, on the outer peripheral surface of the distal portion main body 30, the curved surface portion 53 extends from a portion facing one side (arrow Y1 side) in the second intersecting direction to a portion facing the other side (arrow Y2 side) in the second intersecting direction. Also, on the outer peripheral surface of the distal portion main body 30, the curved surface portion 53 extends between the wall portions 31 and 38 through a portion facing the side (arrow X2 side) opposite to the observing direction of the imaging element.

The curved portion 53 of the distal portion main body 30 is provided with a guide groove 55. The guide groove 55 is recessed inwardly and extends from the proximal side toward the distal side. The guide groove 55 is located on the side (arrow Y1 side) where the observation window 32A (flat surface portion 31A) is located in the second intersecting direction with respect to the longitudinal axis C. The guide groove 55 extends from a distal face to a proximal portion of the distal portion main body 30 along the longitudinal axis C. Also, the guide groove 55 is provided at a position that is approximately 90° away from the flat surface portion 31A around the longitudinal axis C.

A lock pin 57 is fixed to the curved surface portion 53 of the distal portion main body 30. On the curved surface portion 53, the lock pin 57 projects to the outer periphery side. The lock pin 57 is located on the side (arrow Y2 side) opposite to the observation window 32A and the guide groove 55 with respect to the longitudinal axis C, according to the second intersecting direction. Also, the lock pin 57 is provided at a position that is approximately 90° away from the flat surface portion 31A and is approximately 180° away from the guide groove 55 around the longitudinal axis C.

FIGS. 4A to 4C respectively show a structure of the cover 5 to be attached to the distal framing section 23. In FIGS. 4A to 4C, the cover 5 is disassembled into members. The cover 5 has a central axis S, as shown in FIGS. 2 and 4A to 4C. The cover 5 is attached to the distal framing section 23 with the central axis S substantially coaxial with the longitudinal axis C of the insertion section 20. In the present embodiment, the cover 5 is formed of two members, which are a cover main body 60 and a ring member 61 fixed to the proximal side of the cover main body 60. The cover main body 60 and the ring member 61 preferably have electrically insulating properties. The cover main body 60 is preferably formed of plastic. Examples of the plastic forming the cover main body 60 include, but are not limited to, polysulfone, polyethylene, and polycarbonate. The ring member 61 is preferably formed of rubber. Examples of the rubber forming the ring member 61 include, but are not limited to, silicone rubber and fluororubber. In one example, the cover 5 need not be formed of two bodies as described above, but may be formed of one body made of plastic or rubber.

The cover main body 60 includes a distal wall 62 and a peripheral wall 63, and an opening hole 65 for communicating the inside and the outside of the cover main body 60 is formed in the peripheral wall 63. With the opening hole 65, the inner part of the cover 5 is opened in a direction intersecting the central axis S. FIG. 4A shows the cover 5 viewed from a side where the opening hole 65 opens to the outside. With the cover 5 attached to the distal framing section 23, the opening hole 65 is located on the observing direction side of the imaging element (arrow X1 side) with respect to the longitudinal axis C. Namely, with the cover 5 attached to the distal framing section 23, the side where the opening hole 65 opens to the outside substantially coincides with the observing direction of the imaging element. Therefore, with the cover attached to the distal framing section 23, the flat surface portion 31A including the observation window 32A and the illumination window 32B, the cavity 37, the flat surface portion 38A, and the swing table 43 are exposed to the outside of the cover 5 through the opening hole 65. Also, the treatment tool inserted through the channel 40 protrudes from the cavity 37 to the outside of the cover 5 through the opening hole 65.

An engagement groove 67 that is recessed inwardly is formed in a proximal portion of the outer peripheral surface of the cover main body 60. On the outer peripheral surface of the cover main body 60, a flange portion 68 is provided adjacent to the proximal side of the engagement groove 67. The flange portion 68 protrudes to the outer periphery side with respect to the engagement groove 67, and forms a proximal end of the cover main body 60. The engagement groove 67 and the flange portion 68 are formed over the entire circumference around the central axis S. Also, the engagement groove 67 and the flange portion 68 are located on the proximal side (arrow C2 side) with respect to the opening hole 65.

An engagement protrusion 71 protruding inwardly is provided on the inner peripheral surface of the ring member 61. A distal end of the ring member 61 is formed by the engagement protrusion 71. On the inner peripheral surface of the ring member 61, a flange engagement groove 72 is provided adjacent to the proximal side of the engagement protrusion 71. The flange engagement groove 72 is recessed toward the outer periphery side on the inner peripheral surface of the ring member 61. The engagement protrusion 71 engages with the engagement groove 67, and the flange engagement groove 72 engages with the flange portion 68, whereby the ring member 61 is fixed to the cover main body 60. At this time, the engagement of the engagement protrusion 71 with the engagement groove 67 and the engagement of the flange engagement groove 72 with the flange portion 68 restrict the movement of the ring member 61 along the central axis S relative to the cover main body 60, and restrict the movement of the ring member 61 about the central axis S relative to the cover main body 60. With the cover 5 attached to the distal framing section 23, a portion closer to the proximal side than the flange engagement groove 72 on the inner peripheral surface of the ring member 61 abuts, from the outer periphery side, on a thread winding portion 73 (see FIG. 2) provided in a distal portion on the outer peripheral surface of the bending section 25, and is closely contacts thereto in a watertight manner.

A guide protrusion 74 as a cover engagement portion (cover engagement) is provided on the inner peripheral surface of the cover main body 60. The guide protrusion 74 protrudes inwardly and extends from the proximal side toward the distal side. The guide protrusion 74 preferably extends from a proximal portion to a distal portion in the cover main body 60. The guide protrusion 74 is provided at a position that is approximately 90° away from the opening hole 65 around the central axis S. FIG. 4B shows the cover 5 viewed from the side where the guide protrusion 74 is located with respect to the central axis S. When attaching the cover 5 to the distal framing section 23, the guide protrusion 74 is engaged with the guide groove 55 of the distal portion main body 30, and the guide protrusion 74 is moved toward the proximal side in the guide groove 55. Thereby, the cover 5 moves toward the proximal side relative to the distal framing section 23 and is attached to the distal framing section 23. Even in the state where the cover 5 is attached to the distal framing section 23, the guide protrusion 74 engages with the guide groove 55. Therefore, with the cover 5 attached to the distal framing section 23, the guide protrusion 74 is located on the side (arrow Y1 side) where the guide groove 55 and the observation window 32A are located with respect to the longitudinal axis C, in the second intersecting direction. Also, the engagement of the guide protrusion 74 with the guide groove 55 restricts the movement of the cover 5 and the insertion section 20 (distal framing section 23) with respect to each other around the longitudinal axis C (central axis S). Therefore, the guide groove 55 and the guide protrusion 74 position the cover 5 with respect to the distal framing section 23 around the longitudinal axis C.

A lock hole 75 as a cover engagement portion (cover engagement) is formed in the cover main body 60. The lock hole 75 penetrates from the engagement groove 67 to the inside of the cover main body 60. The lock hole 75 is provided at a position that is approximately 90° away from the opening hole 65 and at a position that is approximately 180° away from the guide protrusion 74 around the central axis S. FIG. 4C shows the cover 5 viewed from the side where the lock hole 75 is located with respect to the central axis S. When attaching the cover 5 to the distal framing section 23, the guide protrusion 74 is moved toward the proximal side in the guide groove 55, whereby the cover 5 is moved toward the proximal side relative to the distal framing section 23 up to a position where the portion of the lock pin 57 of the distal framing section 23 projecting toward the outer periphery side can be inserted into the lock hole 75, that is, a position where the lock pin 57 can be engaged with the lock hole 75. Then, with the guide protrusion 74 engaged with the guide groove 55, the lock pin 57 is engaged with the lock hole 75, whereby the cover 5 is attached to the distal framing section 23. Therefore, with the cover 5 attached to the distal framing section 23, the lock hole 75 is located on the side (arrow Y2 side) where the lock pin 57 and the cavity 37 are located with respect to the longitudinal axis C, according to the second intersecting direction. Also, the engagement of the lock pin 57 with the lock hole 75 restricts the movement of the cover 5 and the insertion section 20 (distal framing section 23) with respect to each other along the longitudinal axis C (central axis S). Therefore, the lock pin 57 and the lock hole 75 position the cover 5 with respect to the distal framing section 23 in a direction along the longitudinal axis C.

On the peripheral wall 63 of the cover main body 60, a slit 77A extends from a proximal edge of the opening hole 65 toward the proximal side, and a slit 77B extends from the proximal end of the cover main body 60 toward the distal side. Each of the slits 77A and 77B communicates the outside and the inside of the cover main body 60. Also, the slits 77A and 77B are located at approximately the same angle position as each other around the central axis S, and are located at approximately the same angle position as the opening hole 65 around the central axis S. Therefore, with the cover 5 attached to the distal framing section 23, the slits 77A and 77B are located on the observing direction side of the imaging element (arrow X1 side) with respect to the longitudinal axis C. A distal end of the slit 77A is continuous with the opening hole 65. A proximal end of the slit 77A and a distal end of the slit 77B are not continuous with each other. Providing the slits 77A and 77B decreases the strength of the part between the proximal end of the slit 77A and the distal end of the slit 77B and makes the part between the proximal end of the slit 77A and the distal end of the slit 77B fragile, as compared to other adjacent parts. Namely, a fragile portion 78 having a lower strength than other parts of the cover main body 60 is formed between the proximal end of the slit 77A and the distal end of the slit 77B in the cover main body 60.

When detaching the cover 5 from the distal framing section 23, the fragile portion 78 is broken using, for example, a predetermined jig or by hand, so that the slits 77A and 77B are continuous with each other. Then, the engagement of the lock pin 57 with the lock hole 75 is released using the predetermined jig or by hand. As a result, the guide protrusion 74 can move in the guide groove 55 along the longitudinal axis C. Then, by moving the guide protrusion 74 toward the distal side in the guide groove 55, the cover 5 is moved toward the distal side relative to the distal framing section 23. Thereby, the cover 5 is detached from the distal framing section 23.

In the cover 5, the ring member 61 covers at least a part of the fragile portion 78 from the outer periphery side. Therefore, at least a part of the fragile portion 78 is not exposed to the outside. Therefore, even if the cover 5 abuts on an inner wall of a lumen, for example, during use of the endoscope 3 such as a state of observing the lumen using the endoscope 3 with the cover 5 attached to the distal framing section 23, the breakage of the fragile portion 78 is inhibited.

Figure 5A:
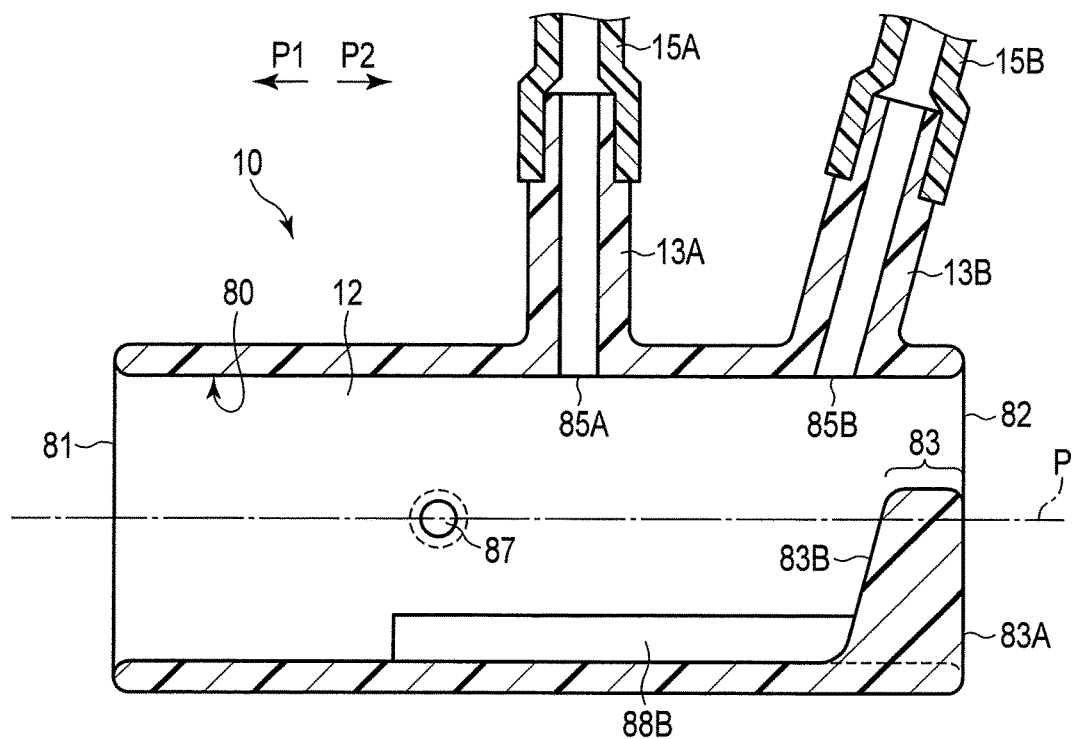
FIG. 5A is a cross-sectional diagram schematically showing a washing tool main body of a washing tool of the first embodiment, as viewed in a cross section substantially parallel with the central axis and passing through connection sleeves.
Figure 5B:
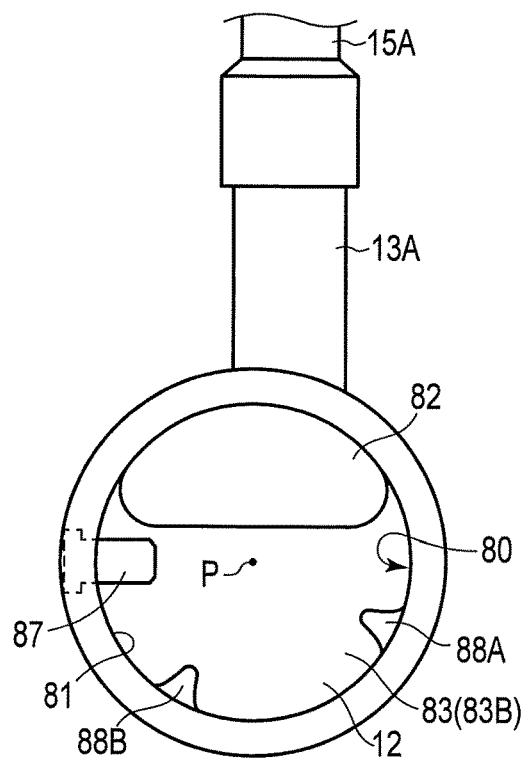
FIG. 5B is a schematic diagram of the washing tool main body of the first embodiment viewed from an insertion opening side.

FIGS. 5A and 5B respectively show a structure of the washing tool main body 10 of the washing tool 2. The washing tool main body 10 has a central axis P, as shown in FIGS. 5A and 5B. The washing tool main body 10 includes an inner peripheral surface 80, and the above-described storage portion (storage cavity) 12 is defined inside the washing tool main body 10 by the inner peripheral surface 80. In the washing tool main body 10, an insertion opening 81 is formed at an end on one side (arrow P1 side) in the direction along the central axis P. In FIG. 5A, the storage portion 12 is opened to the outside of the washing tool main body 10 through the insertion opening 81; however in one example a plurality of opening windows, in addition to the insertion opening 81, may be provided on the periphery of the storage portion 12. Also, in the washing tool main body 10, an opening window 82 is formed at an end on the other side (arrow P2 side) in the direction along the central axis P. The storage portion 12 is opened to the outside of the washing tool main body 10 through the opening window 82. FIG. 5A shows a cross section that is substantially parallel to the central axis P and passes through the connection sleeves 13A and 13B. FIG. 5B shows the washing tool main body 10 viewed from the insertion opening 81 side (arrow P1 side).

The washing tool main body 10 includes a wall portion (wall) 83. The wall portion 83 is provided adjacent to the opening window 82 in a direction intersecting (substantially perpendicular to) the central axis P. The wall portion 83 includes wall surfaces 83A and 83B, and extends toward the insertion opening 81 side from the wall surface 83A to the wall surface 83B along the central axis P. The wall surface 83A faces a side (arrow P2 side) where the opening window 82 opens, and the wall surface 83B faces a side (arrow P1 side) where the insertion opening 81 opens. The wall surface 83A of the wall portion 83 forms an end of the washing tool main body 10 on the opening window 82 side (arrow P2 side) in the direction along the central axis P.

Inflow ports 85A and 85B for allowing a fluid such as a washing liquid to flow into the storage portion 12 are formed in the washing tool main body 10. For example, a fluid supplied through the supply tube 15A flows into the storage portion 12 from the inflow port 85A, and a fluid supplied through the supply tube 15B flows into the storage portion 12 from the inflow port 85B.

A restriction pin 87 is fixed to the washing tool main body 10. The restriction pin (protrusion) 87 on the inner peripheral surface 80 of the washing tool main body 10 protrudes inwardly. The restriction pin 87 is located on the opening window 82 side with respect to the insertion opening 81 and is located on the insertion opening 81 side with respect to the inflow ports 85A and 85B, in a direction along the central axis P. The restriction pin 87 is located at a position that is approximately 90° away from the inflow ports 85A and 85B around the central axis P.

Holding portions (holder) 88A and 88B protruding inwardly are provided on the inner peripheral surface 80 of the washing tool main body 10. Each of the holding portions 88A and 88B extends substantially in parallel with the central axis P. Each of the holding portions 88A and 88B continuously extends, along the central axis P, in a range from substantially the same position as the restriction pin 87 to the wall surface 83B of the wall portion 83. The holding portions 88A and 88B are located opposite to the inflow ports 85A and 85B with respect to the central axis P, in a direction intersecting the central axis P. The holding portions 88A and 88B are spaced apart from each other around the central axis P.

In the washing tool main body 10 with the above-described structure, the cross-sectional area of the storage portion 12, which is substantially perpendicular to the central axis P and ranges from the insertion opening 81 to the restriction pin 87 (ends of the holding portions 88A and 88B on the insertion opening 81 side), is larger than the cross-sectional area of the storage portion 12, which is substantially perpendicular to the central axis P and ranges from the restriction pin 87 to the wall surface 83B of the wall portion 83. Also, the cross-sectional area of the storage portion 12, which is substantially perpendicular to the central axis P and ranges from the restriction pin 87 to the wall surface 83B of the wall portion 83, is larger than the cross-sectional area of the storage portion 12, which is substantially perpendicular to the central axis P and ranges from the wall surface 83B to the opening window 82.

Figure 6:
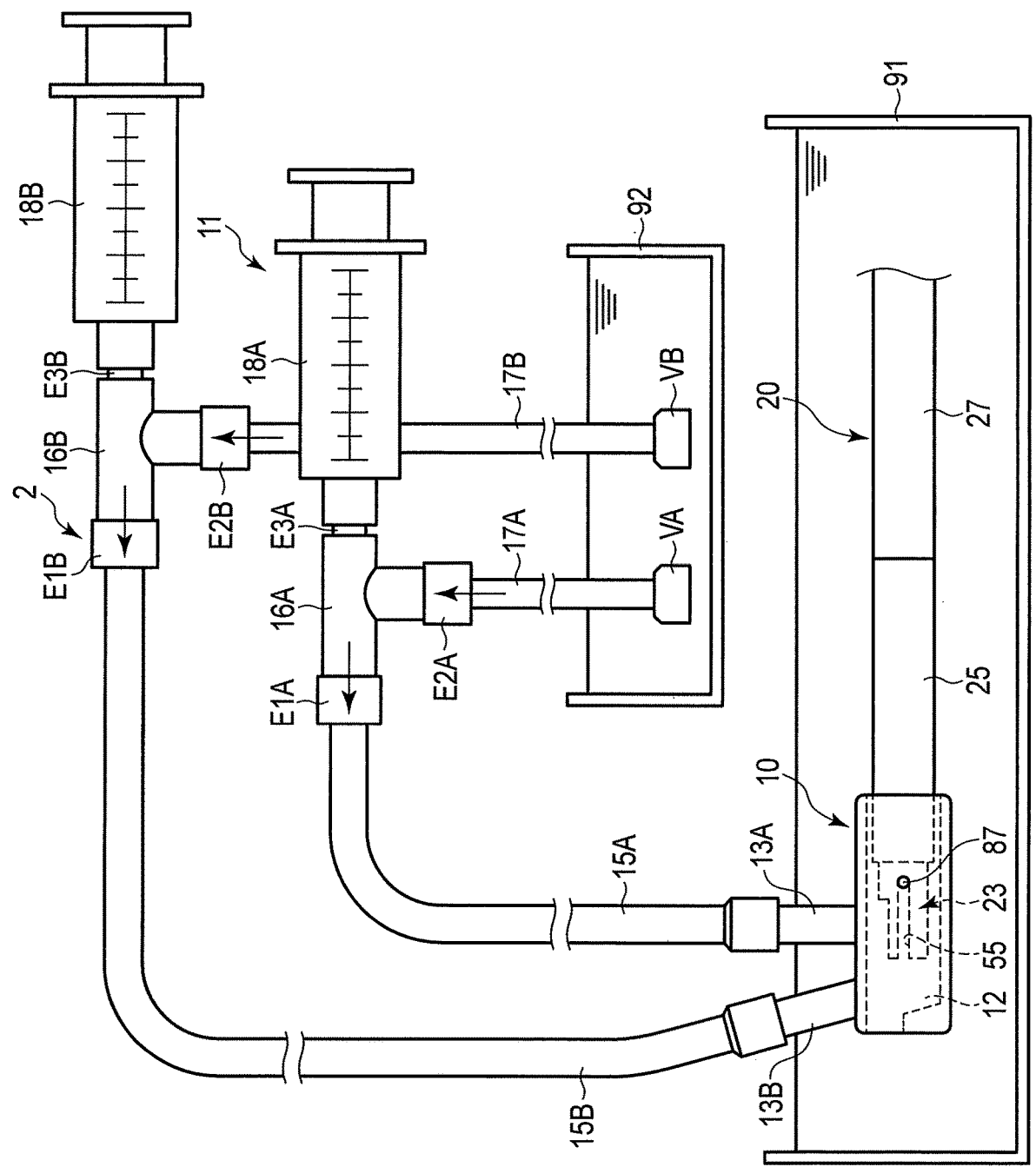
FIG. 6 is a schematic diagram showing a state in which the distal framing section is being washed using the washing tool of the first embodiment.

After using the endoscope 3 with the cover 5 attached to the distal framing section 23, the distal framing section 23 is washed using the washing tool 2. The washing using the washing tool 2 is performed as a preliminary washing before performing a main washing using a washing apparatus for the endoscope, and removes large contaminants. FIG. 6 shows a state in which the distal framing section 23 is being washed using the washing tool 2.

When washing the distal framing section 23, the cover 5 is detached from the distal framing section 23, as described above, and instead of the cover 5, the washing tool main body 10 of the washing tool 2 is attached to the distal framing section 23, as shown in FIG. 6. Then, the distal framing section 23 and the washing tool main body 10 attached to the distal framing section 23 are inserted into a tray 91 filled with a washing liquid. As a result, the distal framing section 23 and the washing tool main body 10 are immersed in the washing liquid in the tray 91. Also, the suction port VA of the suction tube 17A and the suction port VB of the suction tube 17B are immersed in a washing liquid in a tray 92. In this state, the syringe 18A is actuated, whereby the washing liquid as a fluid is supplied from the suction port VA to the inflow port 85A through the suction tube 17A, the branch pipe 16A, and the supply tube 15A in the mentioned order, and flows into the storage portion 12 of the washing tool main body 10 from the inflow port 85A. Also, the syringe 18B is actuated, whereby the washing liquid as a fluid is supplied from the suction port VB to the inflow port 85B through the suction tube 17B, the branch pipe 16B, and the supply tube 15B in the mentioned order, and flows into the storage portion 12 from the inflow port 85B. Then, the distal framing section 23 is washed by the washing liquid having flown into the storage portion 12 from the inflow ports 85A and 85B.

Figure 7A:
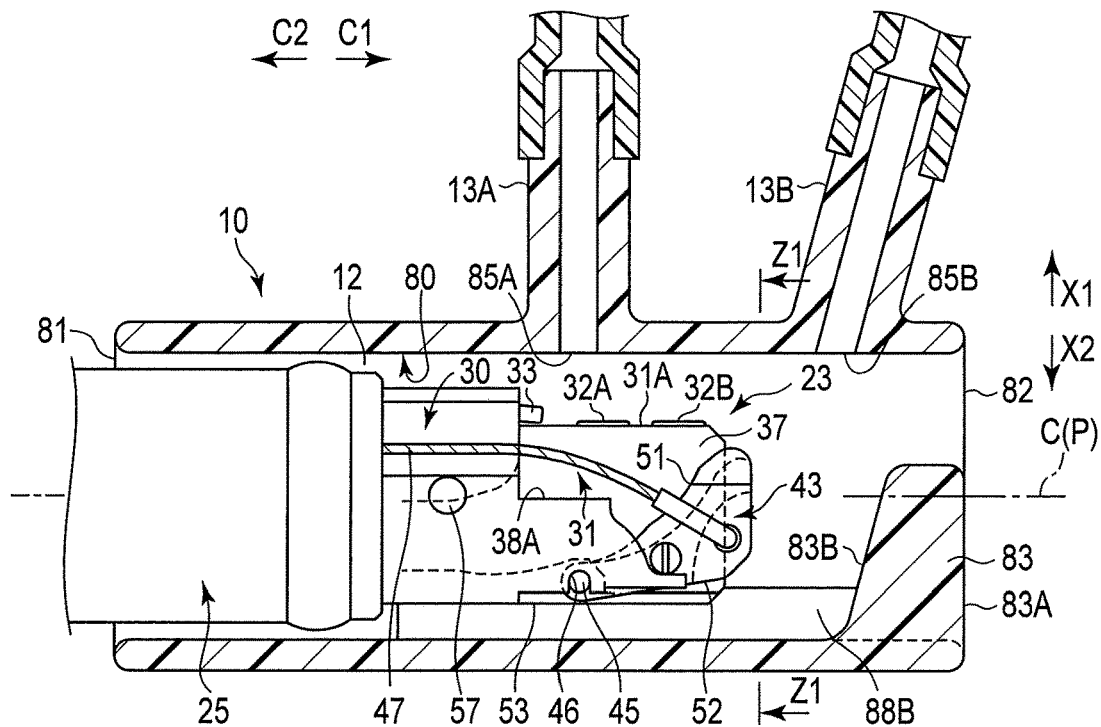
FIG. 7A is a cross-sectional diagram schematically showing a state in which the washing tool main body is attached to the distal framing section of the first embodiment, as viewed in a cross section substantially perpendicular to the second intersecting direction.
Figure 7B:
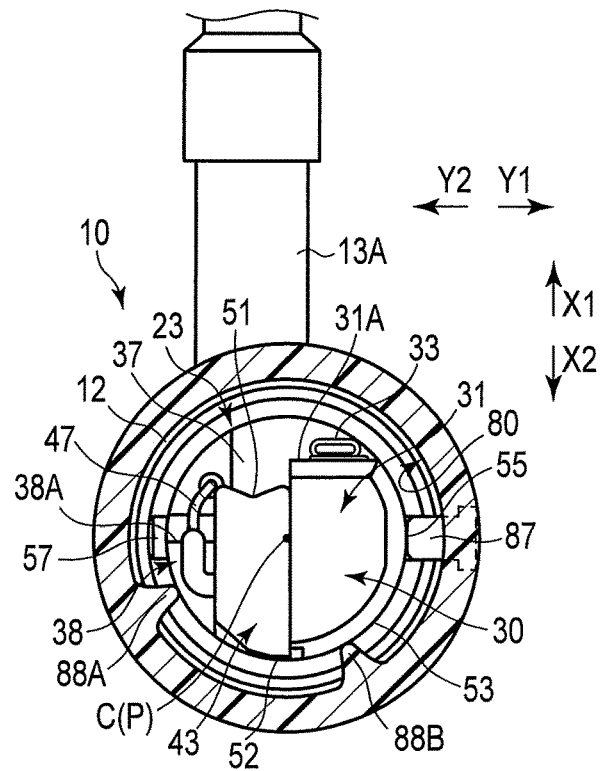
FIG. 7B is a cross-sectional diagram schematically showing a cross section substantially perpendicular to the central axis at position Z1-Z1 in FIG. 7A.

FIGS. 7A and 7B respectively show a state in which the washing tool main body 10 is attached to the distal framing section 23. FIG. 7A shows a cross section that is substantially perpendicular to the second intersecting direction, and FIG. 7B shows a cross section that is substantially perpendicular to the central axis P at position Z1-Z1 in FIG. 7A. When attaching the washing tool main body 10 to the distal framing section 23, the distal framing section 23 is inserted into the storage portion 12 of the washing tool main body 10 from the insertion opening 81 with the swing table 43 lowered, as shown in FIGS. 7A and 7B. Then, the restriction pin (tool engagement portion) 87 of the washing tool main body 10 is engaged with the guide groove (endoscope engagement portion) 55 of the distal portion main body 30. The engagement of the restriction pin 87 with the guide groove 55 restricts the movement of the washing tool main body 10 and the insertion section 20 (distal framing section 23) with respect to each other around the longitudinal axis C (central axis P). Therefore, the restriction pin 87 as a tool engagement portion (tool engagement) positions the washing tool main body 10 with respect to the distal framing section 23 around the longitudinal axis C, so that the restriction pin 87 is at approximately the same angle position as the guide groove 55 as an endoscope engagement portion (endoscope engagement). With the washing tool main body 10 positioned with respect to the distal framing section 23 around the longitudinal axis C, the inflow ports 85A and 85B are located on the observing direction side of the imaging element (arrow X1 side) with respect to the longitudinal axis C, in the first intersecting direction. Therefore, the first surface 51 of the swing table 43 faces the side (arrow X1 side) where the inflow ports 85A and 85B are located with respect to the longitudinal axis C according to the first intersecting direction, and the second surface 52 faces the side (arrow X2 side) opposite to the side where the inflow ports 85A and 85B are located with respect to the longitudinal axis C according to the first intersecting direction.

With the restriction pin 87 engaged with the guide groove 55, the restriction pin 87 is moved from the distal side to the proximal side in the guide groove 55. As a result, the distal framing section 23 moves relative to the washing tool main body 10 from the insertion opening 81 side toward the opening window 82 side in the storage portion 12. The movement of the distal framing section 23 toward the opening window 82 side (distal side) is restricted by the restriction pin 87 abutting on a proximal edge of the guide groove 55. Namely, the restriction pin 87 positions the washing tool main body 10 with respect to the distal framing section 23 in the direction along the longitudinal axis C (central axis P). The distal framing section 23 moves in the storage portion 12 along the longitudinal axis C until the restriction pin 87 abuts on the proximal edge of the guide groove 55, whereby the distal framing section 23 is located at a predetermined position in the storage portion 12 where a fluid such as a washing liquid is supplied. Namely, in the present embodiment, the restriction pin 87 functions as a position adjuster, and defines the position of the distal framing section 23 inside the washing tool main body 10, so that the distal framing section 23 is located at the predetermined position where a fluid is supplied. In the present embodiment, the restriction pin 87 as a position adjuster positions the washing tool main body 10 with respect to the distal framing section 23 in the direction along the longitudinal axis C and a direction around the longitudinal axis C.

Also, in the present embodiment, the guide groove 55 engages with the guide protrusion (cover engagement portion) 74 of the cover 5 when the cover 5 is attached to the distal framing section 23. Therefore, with the structure necessary for attaching the cover 5 to the distal framing section 23, the position of the distal framing section 23 is defined inside the washing tool main body 10, so that the distal framing section 23 is located at the predetermined position. Namely, the washing tool main body 10 is positioned with respect to the distal framing section 23 without complicating the structure of the distal framing section 23.

With the distal framing section 23 located at the predetermined position, the holding portions 88A and 88B abut on the curved surface portion 53 of the distal portion main body 30 from the outer periphery side. As a result, a gap is formed between the inner peripheral surface 80 of the washing tool main body 10 and the outer peripheral portion of the distal framing section 23 in an area other than the restriction pin 87 and the holding portions 88A and 88B. With the distal framing section 23 located at the predetermined position, the support shaft 45 and the shaft receiver 46 are located at substantially the same position as the inflow port 85A in the direction along the longitudinal axis C (central axis P), and are located at substantially the same position as the inflow port 85A in the second intersecting direction. Also, with the distal framing section 23 located at the predetermined position, the distal end of the distal framing section 23 is located on the insertion opening 81 side (proximal side) with respect to the inflow port 85B and the wall portion 83, and a gap is formed between the distal end of the distal framing section 23 and the wall surface 83B of the wall portion 83. In the present embodiment, the distal end of the distal framing section 23 is formed by the swing table 43, and the distal face of the distal portion main body 30 is located closer to the proximal side than the distal end of the distal framing section 23.

FIG. 8 shows a state in which the washing liquid is being supplied to the distal framing section 23 located at the predetermined position in the storage portion 12 of the washing tool main body 10. FIG. 8 shows a cross section that is substantially perpendicular to the second intersecting direction. With the distal framing section 23 located at the predetermined position in the storage portion 12 of the washing tool main body 10, the positional relationship of the support shaft 45 and the shaft receiver 46 with the inflow port 85A is as described above. Therefore, the washing liquid (fluid) having flown into the storage portion 12 from the inflow port 85A is ejected from the first surface 51 toward the support shaft 45 of the swing table 43 and the vicinity thereof (arrow UA in FIG. 8), as shown in FIG. 8. Then, the washing liquid is supplied to the first surface 51 of the swing table 43 and the vicinity thereof. Also, with the distal framing section 23 located at the predetermined position in the storage portion 12 of the washing tool main body 10, the positional relationship of the distal end of the distal framing section 23 with the inflow port 85B and the wall portion 83 is as described above. Therefore, the washing liquid (fluid) having flown into the storage portion 12 from the inflow port 85B passes through the gap between the distal end of the distal framing section 23 and the wall surface 83B of the wall portion 83, and flows into a gap between the second surface 52 of the swing table 43 and the inner peripheral surface 80 of the washing tool main body 10 (arrow UB in FIG. 8). As a result, the washing liquid is supplied to the second surface 52 of the swing table 43 and the vicinity thereof. With the distal framing section 23 located at the predetermined position in the storage portion 12, the washing liquid is supplied to both the first surface 51 and the second surface 52 of the swing table 43, as described above. Therefore, the swing table 43 is properly washed.

The washing tool main body 10 is provided with the insertion opening 81 and the opening window 82 that opens on a side opposite to the insertion opening 81. Therefore, a drained liquid easily flows out from the storage portion 12 inside the washing tool main body 10 to the outside of the washing tool main body 10 through the insertion opening 81 or the opening window 82, and hardly accumulates in the storage portion 12.

Also, with the cover 5 unattached to the distal framing section 23, the swing table 43 and the support shaft 45 can be slightly moved on the shaft receiver 46 relative to the distal portion main body 30 in a direction intersecting the central axis of the support shaft 45. Therefore, ejecting a fluid from the inflow port 85A to the support shaft 45 and the vicinity thereof makes the support shaft 45 slightly move relative to the shaft receiver 46 by the fluid pressure. Also, with the distal framing section 23 located at the predetermined position in the storage portion 12 of the washing tool main body 10, a distance W2 between the second surface 52 of the swing table 43 and the inner peripheral surface 80 of the washing tool main body 10 is smaller than a distance W1 between the distal end of the distal framing section 23 and the wall surface 83B of the wall portion 83. Therefore, a flow rate of the fluid passing between the second surface 52 of the swing table 43 and the inner peripheral surface 80 of the washing tool main body 10 is larger than a flow rate of the fluid passing between the distal end of the distal framing section 23 and the wall surface 83B of the wall portion 83. As the flow rate of the fluid passing between the second surface 52 and the inner peripheral surface 80 increases, the support shaft 45 slightly moves relative to the shaft receiver 46 by the fluid pressure. Therefore, in the present embodiment, the support shaft 45 and the swing table 43 are slightly moved relative to the shaft receiver 46 by the washing liquid having flown in from the inflow ports 85A and 85B, so that the support shaft 45 is spaced from the shaft receiver 46. As the support shaft 45 is spaced from the shaft receiver 46, a gap is formed between the distal portion main body (distal frame main body) 30, which forms the shaft receiver 46, and the support shaft 45. As a result, the support shaft 45 and the vicinity thereof are properly washed, and the swing table 43 is also properly washed.

Figure 9B:
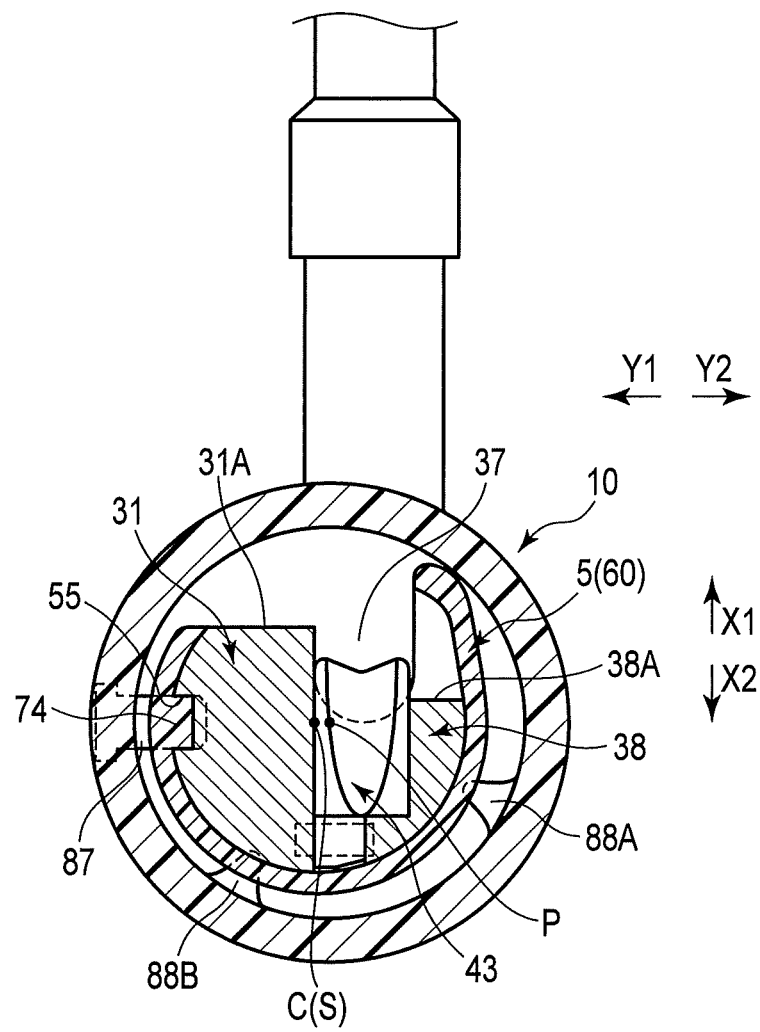
FIG. 9B is a cross-sectional diagram schematically showing a state in which the distal framing section with the cover of the first embodiment attached thereto is inserted in the storage portion of the washing tool main body, as viewed in a cross section substantially perpendicular to the longitudinal axis and passing through the distal framing section and the cover.

FIGS. 9A and 9B respectively show a state in which the distal framing section 23 with the cover 5 attached thereto is inserted into the storage portion 12 of the washing tool main body 10. FIG. 9A shows a cross section that is substantially perpendicular to the second intersecting direction, and FIG. 9B shows a cross section that is substantially perpendicular to the longitudinal axis C and passes through the distal framing section 23 and the cover 5. As shown in FIG. 9A, when the distal framing section 23 is inserted into the storage portion 12 from the insertion opening 81 with the cover 5 attached to the distal framing section 23, a distal portion of the cover 5 abuts on the restriction pin 87 or the ends of the holding portions 88A and 88B on the insertion opening 81 side, and interferes with the restriction pin 87, or the holding portions 88A and 88B. As a result, the movement of the distal framing section 23 and the cover 5 from the restriction pin 87 (the ends of the holding portions 88A and 88B on the insertion opening 81 side) toward the opening window 82 side (distal side) is restricted. Since the cover 5 and the distal framing section 23 cannot move from the restriction pin 87 toward the opening window 82 side in the storage portion 12, the distal framing section 23 with the cover 5 attached thereto cannot move to the aforementioned predetermined position in the storage portion 12. Namely, in the present embodiment, the restriction pin 87 and the holding portions 88A and 88B function as regulators, and the restriction pin 87 and the holding portions 88A and 88B interfere with the cover 5, thereby restricting the movement of the distal framing section 23 with the cover 5 attached thereto to the predetermined position. In the present embodiment, the restriction pin (protrusion) 87 as a position adjuster also functions as a regulator. In addition, restricting the movement to the predetermined position includes restraining the movement to the predetermined position, and means limiting the movement to the predetermined position.

With the above-described structure, the distal framing section 23 cannot be moved to the predetermined position in the storage portion 12 when the distal framing section 23 is washed using the washing tool 2 without detaching the cover 5 from the distal framing section 23 after using the endoscope 3. Therefore, a user can properly recognize that the cover 5 is not detached from the distal framing section 23. Accordingly, in the present embodiment, only with the cover 5 detached from the distal framing section 23, the distal framing section 23 can be located at the predetermined position in the storage portion 12 where the washing liquid (fluid) is properly supplied. This reliably prevents the distal framing section 23 from being washed with the cover 5 attached to the distal framing section 23. Only with the cover 5 detached from the distal framing section 23, the user can recognize that the distal framing section 23 is disposed at the predetermined position in the storage portion 12 to be washed. Completely washing the distal framing section 23 with the cover 5 detached from the distal framing section 23 allows the detailed parts of the distal framing section 23, for example, around the swing table (raising base) 43 to be easily and completely washed.

Modifications

In a first modification shown in FIGS. 10A and 10B, a guide surface 93 is provided as an endoscope engagement portion (endoscope engagement) instead of the guide groove 55. The guide surface 93 extends from the proximal side toward the distal side, and is located on the side (arrow Y1 side) where the observation window 32A (flat portion 31A) is located with respect to the longitudinal axis C, in the second intersecting direction. Also, the guide surface 93 has a flat shape and faces one side (arrow Y1 side) in the second intersecting direction. The guide surface 93 is provided at a position that is approximately 90° away from the flat surface portion 31A around the longitudinal axis C. A step surface 95 that faces the distal side (arrow C1 side) is formed at a proximal end of the guide surface 93. FIG. 10A shows the distal framing section 23 viewed from one side in the second intersecting direction. FIG. 10B shows a state in which the washing tool main body 10 is attached to the distal framing section 23, as viewed in a cross section that is substantially perpendicular to the longitudinal axis C (central axis P) and passes through a position located on the opening window 82 side with respect to the distal end of the distal framing section 23.

In the present modification, when attaching the washing tool main body 10 to the distal framing section 23, the restriction pin (tool engagement portion) 87 of the washing tool main body 10 is engaged with the guide surface (endoscope engagement portion) 93 of the distal portion main body 30. Namely, a protruding end of the restriction pin 87 is brought into contact with the guide surface 93 from the outer periphery side. As a result, the restriction pin 87 as a tool engagement portion (tool engagement) positions the washing tool main body 10 with respect to the distal framing section 23 around the longitudinal axis C, so that the restriction pin 87 is located at approximately the same angle position as the guide surface 93 as an endoscope engagement portion.

With the restriction pin 87 engaged with the guide surface 93, namely, with the restriction pin 87 abutting on the guide surface 93, the restriction pin 87 is moved from the distal side to the proximal side on the guide surface 93. As a result, the distal framing section 23 moves relative to the washing tool main body 10 from the insertion opening 81 side toward the opening window 82 side in the storage portion 12. The movement of the distal framing section 23 toward the opening window 82 side (distal side) is restricted by the restriction pin 87 abutting on the step surface 95 at the proximal end of the guide surface 93. Namely, the restriction pin 87 positions the washing tool main body 10 with respect to the distal framing section 23 in the direction along the longitudinal axis C (central axis P). The distal framing section 23 moves in the storage portion 12 along the longitudinal axis C until the restriction pin 87 abuts on the step surface 95, whereby the distal framing section 23 is located at the predetermined position in the storage portion 12 where a fluid such as a washing liquid is supplied. Accordingly, in the present modification as well, the restriction pin 87 functions as a position adjuster, and defines the position of the distal framing section 23 inside the washing tool main body 10, so that the distal framing section 23 is located at the predetermined position where a fluid is supplied.

In the present modification, as in the first embodiment, the restriction pin 87 and the holding portions 88A and 88B function as regulators, and the restriction pin 87 and the holding portions 88A and 88B interfere with the cover 5, thereby restricting the movement of the distal framing section 23 with the cover 5 attached thereto to the predetermined position.

In a second modification shown in FIGS. 11A to 13B, a restriction protruding portion (restriction protrusion) 100 is provided instead of the restriction pin 87 as a tool engagement portion (tool engagement). The restriction protruding portion 100 on the inner peripheral surface 80 of the washing tool main body 10 protrudes inwardly. The restriction protruding portion 100 is located at approximately the same angle position as the inflow ports 85A and 85B around the central axis P. The inflow port 85A is formed at a protruding end of the restriction protruding portion 100. Also, the restriction protruding portion 100 is located on the insertion opening 81 side with respect to the inflow port 85B and the wall portion 83 in the direction along the central axis P.

The restriction protruding portion 100 includes a protruding side face 101A facing the insertion opening 81 side and a protruding side face 101B facing the opening window 82 side. The restriction protruding portion 100 also includes protruding end faces 102A and 102B facing the inner periphery side. The protruding end faces 102A and 102B are provided adjacent to each other in the direction intersecting the central axis P. A step surface 103 is formed between the protruding end faces 102A and 102B. Because of the step surface 103, the protruding end face 102A is located on the inner periphery side with respect to the protruding end face 102B.

Figure 11A:
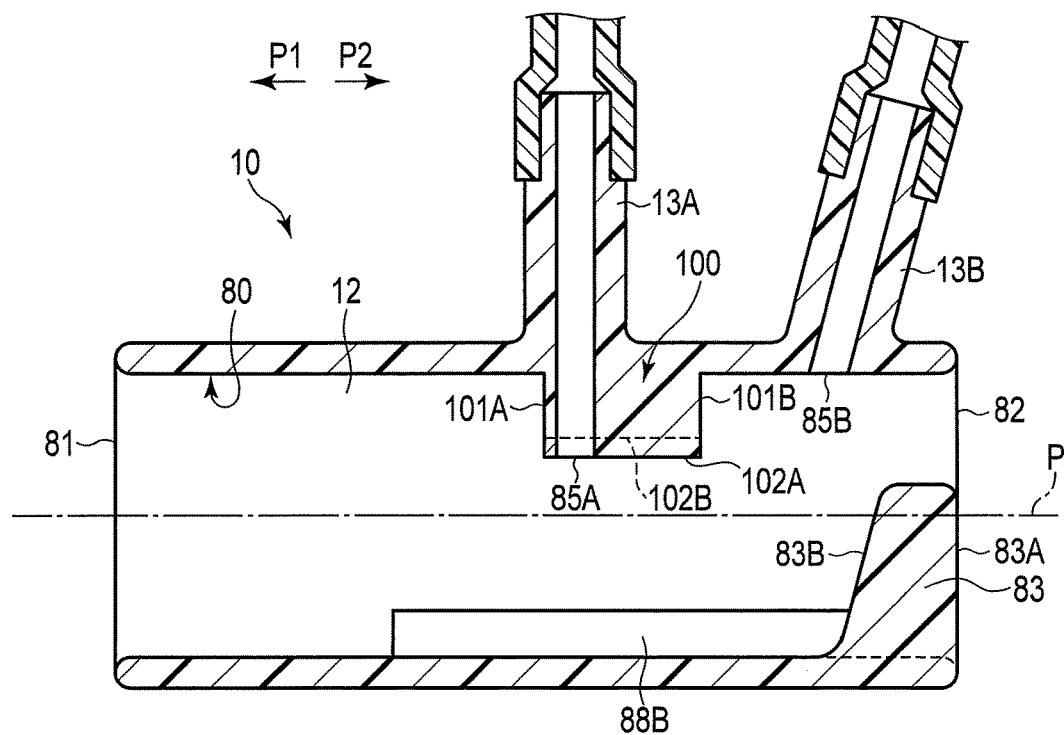
FIG. 11A is a cross-sectional diagram schematically showing a washing tool main body of a second modification, as viewed in a cross section substantially parallel with the central axis and passing through connection sleeves.
Figure 11B:
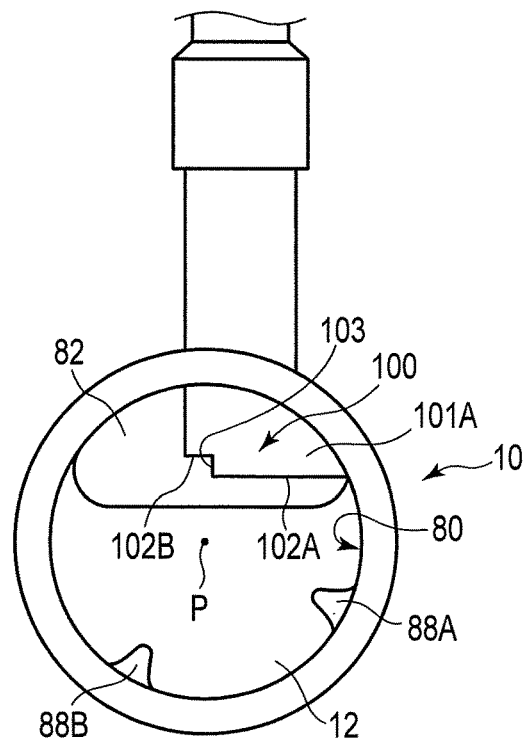
FIG. 11B is a schematic diagram of the washing tool main body of the second modification viewed from the insertion opening side.

FIG. 11A shows the washing tool main body 10 as viewed in a cross section substantially parallel to the central axis P and passing through the connection sleeves 13A and 13B. FIG. 11B shows the washing tool main body 10 viewed from the insertion opening 81 side. FIGS. 12A and 12B respectively show a state in which the washing tool main body 10 is attached to the distal framing section 23. FIG. 12A shows a cross section substantially perpendicular to the second intersecting direction. FIG. 12B shows a cross section substantially perpendicular to the longitudinal axis C and passing through the distal framing section 23. FIGS. 13A and 13B respectively show a state in which the distal framing section 23 with the cover 5 attached thereto is inserted into the storage portion 12 of the washing tool main body 10. FIG. 13A shows a cross section substantially perpendicular to the second intersecting direction. FIG. 13B shows a cross section substantially perpendicular to the longitudinal axis C and passing through the distal framing section 23 and the cover 5.

In the present modification as well, when attaching the washing tool main body 10 to the distal framing section 23, the distal framing section 23 is inserted into the storage portion 12 of the washing tool main body 10 from the insertion opening 81 in a state where the swing table 43 is lowered. At this time, the distal framing section 23 is moved toward the opening window 82 side in a state where the restriction protruding portion 100 is located on the observing direction side of the imaging element (arrow X1 side) with respect to the longitudinal axis C, in the first intersecting direction. Therefore, with the distal framing section 23 moved toward the opening window 82 in the range where the restriction protruding portion 100 is provided, the flat surface portion 38A of the wall portion 38 and the first surface 51 of the swing table 43 face the protruding end face 102A, and a part of the flat surface portion 31A of the wall portion 31 faces the protruding end face 102B. At this time, the wall portion 31 is located on the side (arrow Y1 side) where the protruding end face 102B is located with respect to the step surface 103 of the restriction protruding portion 100, as viewed in the second intersecting direction. The wall portion 38 and the swing table 43 are located on the side (arrow Y2 side) where the protruding end face 102A is located with respect to the step surface 103 of the restriction protruding portion 100, according to the second intersecting direction.

Also, with the distal framing section 23 having moved in the storage portion 12 toward the opening window 82 side to reach the area where the restriction protruding portion 100 is provided, the wall portion 31 abuts on the protruding end face 102B or the step surface 103, or the swing table 43 or the wall portion 38 abut on the protruding end face 102A, thereby restricting the movement of the distal framing section 23 relative to the washing tool main body 10 around the longitudinal axis C (central axis P). Therefore, the restriction protruding portion 100 positions the washing tool main body 10 with respect to the distal framing section 23 around the longitudinal axis C, so that the restriction protruding portion 100 is located on the observing direction side of the imaging element (arrow X1 side) with respect to the longitudinal axis C. In the present modification as well, with the washing tool main body 10 positioned with respect to the distal framing section 23 around the longitudinal axis C, the first surface 51 of the swing table 43 faces the side (arrow X1 side) where the inflow ports 85A and 85B are located with respect to the longitudinal axis C in the first intersecting direction, and the second surface 52 faces the side (arrow X2 side) opposite to the side where the inflow ports 85A and 85B are located with respect to the longitudinal axis C in the first intersecting direction.

With the movement of the distal framing section 23 relative to the washing tool main body 10 around the longitudinal axis C restricted by the restriction protruding portion 100, the distal framing section 23 moves relative to the washing tool main body 10 from the insertion opening 81 side toward the opening window 82 side in the storage portion 12. In the present modification, a distal face 105 of the bending section 25 abuts on the ends of the holding portions 88A and 88B on the insertion opening 81 side (proximal side), thereby restricting the movement of the distal framing section 23 toward the opening window 82 side (distal side). Namely, the holding portions 88A and 88B position the washing tool main body 10 with respect to the distal framing section 23 in the direction along the longitudinal axis C (central axis P).

The movement of the distal framing section 23 relative to the washing tool main body 10 around the longitudinal axis C is restricted by the restriction protruding portion 100, and the distal framing section 23 moves in the storage portion 12 along the longitudinal axis C until the distal face 105 of the bending section 25 abuts on one end of the holding portions 88A and 88B, whereby the distal framing section 23 is located at the predetermined position in the storage portion 12 where a fluid such as a washing liquid is supplied. Namely, in the present modification, the restriction protruding portion 100 and the holding portions 88A and 88B function as position adjusters, and define the position of the distal framing section 23 inside the washing tool main body 10, so that the distal framing section 23 is located at the predetermined position where a fluid is supplied.

Also, in the present modification, when the distal framing section 23 is inserted into the storage portion 12 from the insertion opening 81 with the cover 5 attached to the distal framing section 23, the distal portion of the cover 5 abuts on the protruding side face 101A of the restriction protruding portion 100 or the holding portions 88A and 88B, and interferes with the restriction protruding portion 100 or the holding portions 88A and 88B. As a result, the movement of the distal framing section 23 and the cover 5 from the protruding side face 101A of the restriction protruding portion 100 toward the opening window 82 side (distal side) is restricted. Since the cover 5 and the distal framing section 23 cannot move from the protruding side face 101A toward the opening window 82 side in the storage portion 12, the distal framing section 23 with the cover 5 attached thereto cannot move to the aforementioned predetermined position in the storage portion 12. Namely, in the present modification, the restriction protruding portion 100 and the holding portions 88A and 88B function as regulators, and the restriction protruding portion 100 and the holding portions 88A and 88B interfere with the cover 5, thereby restricting the movement of the distal framing section 23 with the cover 5 attached thereto to the predetermined position. In the present modification, the restriction protruding portion 100 and the holding portions 88A and 88B as position adjusters also function as regulators.

Also, in the present modification, a distal portion of the swing table 43 interferes with the restriction protruding portion 100 in a state where the swing table 43 is raised, that is, in a state where the swing table 43 is not lowered. As a result, the movement of the distal framing section 23 with the raised swing table 43 from the protruding side face 101A of the restriction protruding portion 100 toward the opening window 82 side (distal side) is restricted. Since the distal framing section 23 cannot move from the protruding side face 101A toward the opening window 82 side in the storage portion 12, the distal framing section 23 cannot move to the aforementioned predetermined position in the storage portion 12 when the swing table 43 is not lowered. Therefore, in the present modification, the washing tool main body 10 is attached to the distal framing section 23 only with the swing table 43 lowered.

In a third modification shown in FIGS. 14A to 16B, a restriction inner peripheral surface 106 is provided instead of the restriction pin 87 as a tool engagement portion. The restriction inner peripheral surface 106 forms a part of the inner peripheral surface 80 of the washing tool main body 10 and is formed over the entire circumference around the central axis P. The restriction inner peripheral surface 106 extends from the opening window 82 toward the insertion opening 81 side. The restriction inner peripheral surface 106 protrudes inwardly, as compared to the portion of the inner peripheral surface 80 that is located on the insertion opening 81 side with respect to the restriction inner peripheral surface 106. Therefore, a step surface 112 is formed at an end of the restriction inner peripheral surface 106 on the insertion opening 81 side in the direction along the central axis P. The step surface 112 is formed over the entire circumference around the central axis P. The inflow ports 85A and 85B are provided on the restriction inner peripheral surface 106. Therefore, the step surface 112 (end of the restriction inner peripheral surface 106 on the insertion opening 81 side) is located on the insertion opening 81 side (arrow P1 side) with respect to the inflow port 85A in the direction along the central axis P.

The cross-sectional shape of the restriction inner peripheral surface 106 that is substantially perpendicular to the central axis P is substantially D-shaped from the end of the restriction inner peripheral surface 106 on the insertion opening 81 side to the opening window 82. Namely, the restriction inner peripheral surface 106 includes a curved surface portion (curved surface) 107 and a flat surface portion (flat surface) 108, and both ends of the curved surface portion 107 are continuous with the flat surface portion 108 in the cross section substantially perpendicular to the central axis P. The inflow ports 85A and 85B are formed on the flat surface portion 108. The curved surface portion 107 is formed in an arc shape having a radius RO with the longitudinal axis P substantially in the center, when viewed in the cross section substantially perpendicular to the longitudinal axis P, and the radius RO is approximately equal to the distance from the longitudinal axis C to the curved surface portion 53 of the distal portion main body 30.

A protruding portion (protrusion) 111 protruding inwardly from the curved surface portion 107 is provided on the restriction inner peripheral surface 106. The protruding portion 111 extends from the opening window 82 toward the insertion opening 81 side. The end of the protruding portion 111 on the insertion opening 81 side is located on the opening window 82 side (arrow P2 side) with respect to the step surface 112 and the inflow port 85A in the direction along the central axis P. The end of the protruding portion 111 on the insertion opening 81 side is located on the insertion opening 81 side (arrow P1 side) with respect to the inflow port 85B in the direction along the central axis P. Also, the protruding portion 111 is located at a position that is approximately 180° away from the flat surface portion 108 and the inflow ports 85A and 85B around the central axis P.

FIG. 14A shows the washing tool main body 10 as viewed in a cross section substantially parallel to the central axis P and passing through the connection sleeves 13A and 13B. FIG. 14B shows the washing tool main body 10 viewed from the insertion opening 81 side. FIGS. 15A and 15B respectively show a state in which the washing tool main body 10 is attached to the distal framing section 23.

FIG. 15A shows a cross section substantially perpendicular to the second intersecting direction. FIG. 15B shows a cross section substantially perpendicular to the longitudinal axis C and passing through the distal framing section 23. FIGS. 16A and 16B respectively show a state in which the distal framing section 23 with the cover 5 attached thereto is inserted into the storage portion 12 of the washing tool main body 10. FIG. 16A shows a cross section substantially perpendicular to the second intersecting direction. FIG. 16B shows a cross section substantially perpendicular to the longitudinal axis C and passing through the distal framing section 23 and the cover 5.

In the present modification as well, when attaching the washing tool main body 10 to the distal framing section 23, the distal framing section 23 is inserted into the storage portion 12 of the washing tool main body 10 from the insertion opening 81. At this time, the distal framing section 23 is moved toward the opening window 82 side with the flat surface portion 108 located on the observing direction of the imaging element (arrow X1 side) with respect to the longitudinal axis C, in the first intersecting direction. Therefore, with the distal framing section 23 moved toward the opening window 82 in the range where the restriction inner peripheral surface 106 is provided, the curved surface portion 107 abuts on the curved surface portion 53 of the distal portion main body 30 from the outer periphery side, and the flat surface portion 108 abuts on the flat surface portion 31A of the wall portion 31 from the outer periphery side. With the distal framing section 23 having moved in the storage portion 12 toward the opening window 82 side to reach the area where the restriction inner peripheral surface 106 is provided, the movement of the distal framing section 23 relative to the washing tool main body 10 around the longitudinal axis C (central axis P) is restricted by the substantially D-shaped cross-sectional shape of the restriction inner peripheral surface 106 perpendicular to the longitudinal axis C (central axis P). Therefore, the restriction inner peripheral surface 106 positions the washing tool main body 10 with respect to the distal framing section 23 around the longitudinal axis C, so that the flat surface portion 108 is located on the observing direction side of the imaging element (arrow X1 side) with respect to the longitudinal axis C. In the present modification as well, with the washing tool main body 10 positioned with respect to the distal framing section 23 around the longitudinal axis C, the first surface 51 of the swing table 43 faces the side (arrow X1 side) where the inflow ports 85A and 85B are located with respect to the longitudinal axis C according to the first intersecting direction, and the second surface 52 faces the side (arrow X2 side) opposite to the side where the inflow ports 85A and 85B are located with respect to the longitudinal axis C according to the first intersecting direction.

With the movement of the distal framing section 23 relative to the washing tool main body 10 around the longitudinal axis C restricted by the restriction inner peripheral surface 106, the distal framing section 23 moves relative to the washing tool main body 10 from the insertion opening 81 side toward the opening window 82 side in the storage portion 12. In the present modification, a distal face 113 of the distal portion main body 30 abuts on the end of the protruding portion 111 on the insertion opening 81 side (proximal side), thereby restricting the movement of the distal framing section 23 toward the opening window 82 side (distal side). Namely, the protruding portion 111 positions the washing tool main body 10 with respect to the distal framing section 23 in the direction along the longitudinal axis C (central axis P). In the present modification as well, the distal end of the distal framing section 23 is formed by a distal end of the swing table 43, and the distal face 113 of the distal portion main body 30 is located on the proximal side with respect to the distal end of the swing table 43.

The movement of the distal framing section 23 relative to the washing tool main body 10 around the longitudinal axis C is restricted by the restriction inner peripheral surface 106, and the distal framing section 23 moves in the storage portion 12 along the longitudinal axis C until the distal face 113 of the distal portion main body 30 abuts on one end of the protruding portion 111, whereby the distal framing section 23 is located at the predetermined position in the storage portion 12 where a fluid such as a washing liquid is supplied. Namely, in the present modification, the restriction inner peripheral surface 106 and the protruding portion 111 function as position adjusters, and define the position of the distal framing section 23 inside the washing tool main body 10, so that the distal framing section 23 is located at the predetermined position where a fluid is supplied.

When the swing table 43 is raised as indicated by the two-dot chain line in FIG. 15A with the distal framing section 23 located at the aforementioned predetermined position in the storage portion 12, the swing table 43 abuts on the flat surface portion 108 of the restriction inner peripheral surface 106. As a result, the movement of the distal framing section 23 from the predetermined position toward the insertion opening 81 side is suppressed. Therefore, the distal framing section 23 is prevented from moving from the predetermined position toward the insertion opening 81 side due to liquid pressure or the like when being washed by the washing liquid having flown in from the inflow ports 85A and 85B. Upon completion of the washing, the swing table 43 is lowered, as indicated by the solid line in FIG. 15A. As a result, the swing table 43 does not come into contact with the flat surface portion 108, and the distal framing section 23 can move toward the insertion opening 81 side relative to the washing tool main body 10. Therefore, the washing tool main body 10 can be detached from the distal framing section 23.

Also, in the present modification, when the distal framing section 23 is inserted into the storage portion 12 from the insertion opening 81 with the cover 5 attached to the distal framing section 23, the distal portion of the cover 5 abuts on the end of the restriction inner peripheral surface 106 on the insertion opening 81 side, that is, the step surface 112, and interferes with the step surface 112. As a result, the movement of the distal framing section 23 and the cover 5 from the step surface 112 toward the opening window 82 side (distal side) is restricted. Since the cover 5 and the distal framing section 23 cannot move from the step surface 112 toward the opening window 82 side in the storage portion 12, the distal framing section 23 with the cover 5 attached thereto cannot move to the aforementioned predetermined position in the storage portion 12. Namely, in the present modification, the step surface 112 functions as a regulator, and the step surface 112 interferes with the cover 5, thereby restricting the movement of the distal framing section 23 with the cover 5 attached thereto to the predetermined position.

Figure 17A:
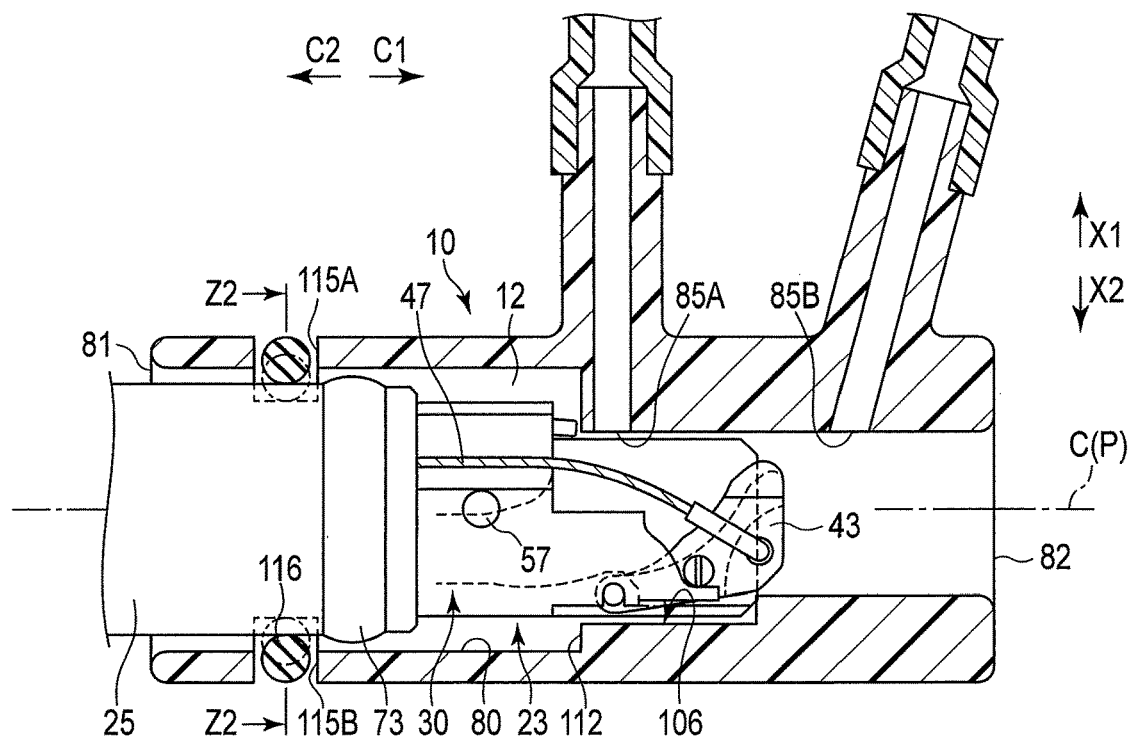
FIG. 17A is a cross-sectional diagram schematically showing a state in which the washing tool main body is attached to a distal framing section of a fourth modification, as viewed in a cross section substantially perpendicular to the second intersecting direction.
Figure 17B:
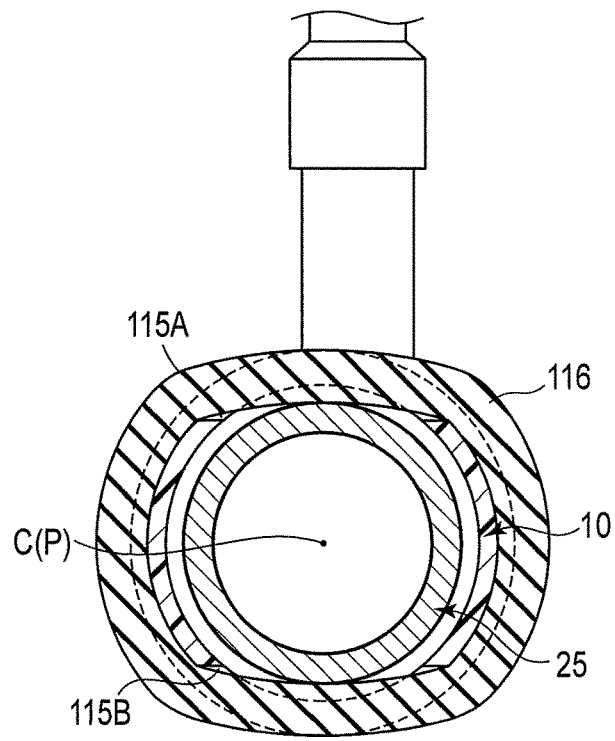
FIG. 17B is a cross-sectional diagram schematically showing a cross section substantially perpendicular to the longitudinal axis at position Z2-Z2 in FIG. 17A.

In a fourth modification shown in FIGS. 17A and 17B, the washing tool main body 10 is provided with cuts 115A and 115B, in addition to the structure similar to that of the third modification. Each of the cuts 115A and 115B penetrates from the outside of the washing tool main body 10 to the storage portion 12. The cuts 115A and 115B are provided at substantially the same position in the direction along the central axis P, and are arranged approximately 180° away from each other around the central axis P (longitudinal axis C). Also, the cuts 115A and 115B are located on the insertion opening 81 side with respect to the step surface 112 (the end of the restriction inner peripheral surface 106 on the insertion opening 81 side) in the direction along the central axis P. In the present modification, an O-ring 116 as an elastic member is attached to the cuts 115A and 115B. The elastic member attached to the cuts 115A and 115B is not limited to the O-ring 116 as long as it is a ring-shaped member. FIG. 17A shows a state in which the washing tool main body 10 is attached to the distal framing section 23, as viewed in a cross section substantially perpendicular to the second intersecting direction. FIG. 17B shows a cross section substantially perpendicular to the longitudinal axis C at position Z2-Z2 in FIG. 17A.

In the present modification, with the distal framing section 23 located at the aforementioned predetermined position in the storage portion 12, the thread winding portion 73 provided in the distal portion of the outer peripheral surface of the bending section 25 is located between the O-ring 116 and the step surface 112 in the direction along the central axis P. Therefore, when moving the distal framing section 23 from the insertion opening 81 to the predetermined position, the thread winding portion 73 moves toward the opening window 82 side in the range where the O-ring 116 is provided. The distance from the longitudinal axis C to the outer peripheral surface in the thread winding portion 73, that is, the outer diameter of the thread winding portion 73 is larger than that of the distal framing section 23. Therefore, the O-ring 116 elastically deforms as the thread winding portion 73 moves toward the opening window 82 side in the range where the O-ring 116 is provided. Due to the elastic deformation of the O-ring 116, the operator can obtain a click feeling. Based on the presence or absence of the click feeling, the operator can determine whether or not the distal framing section 23 has moved to the aforementioned predetermined position in the storage portion 12.

With the distal framing section 23 located at the aforementioned predetermined position in the storage portion 12, the O-ring 116 suppresses the movement of the thread winding portion 73 in the storage portion 12 toward the insertion opening 81 side relative to the O-ring 116. As a result, the distal framing section 23 is prevented from moving from the predetermined position toward the insertion opening 81 side due to liquid pressure or the like when being washed by the washing liquid having flown in from the inflow ports 85A and 85B. Therefore, the distal framing section 23 is prevented from moving unintentionally toward the insertion opening 81 side.

Figure 18A:
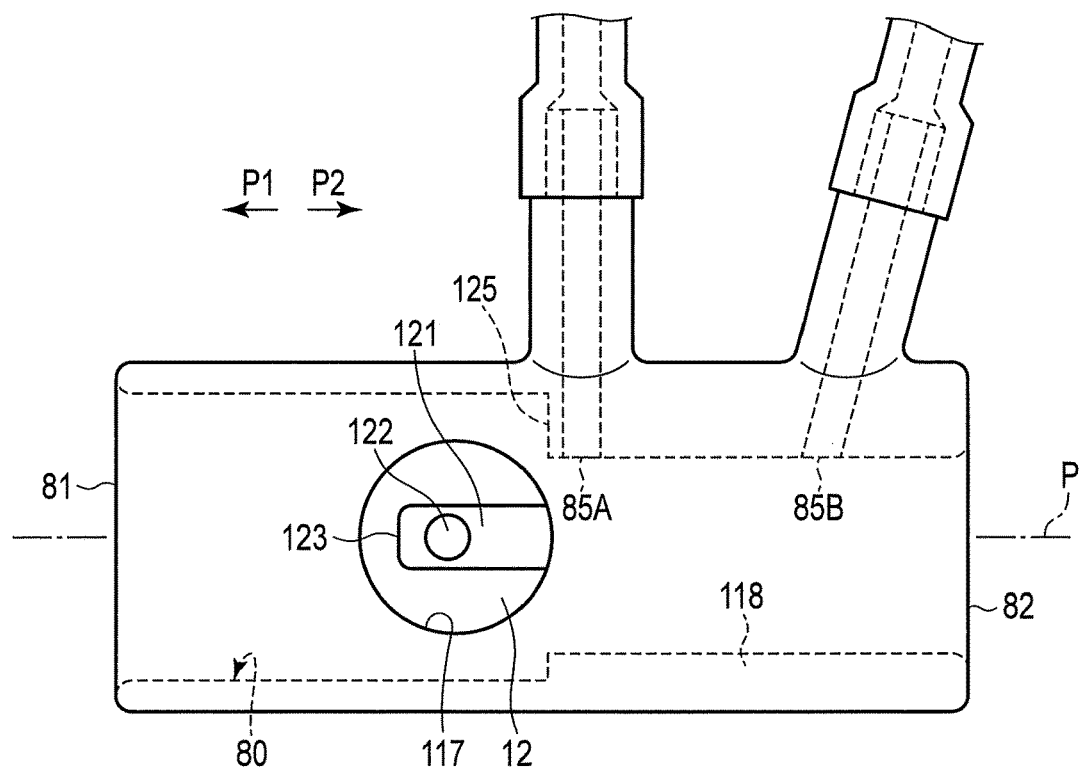
FIG. 18A is a schematic diagram of a washing tool main body of a fifth modification viewed from a side where the opening window is located with respect to the central axis.
Figure 18B:
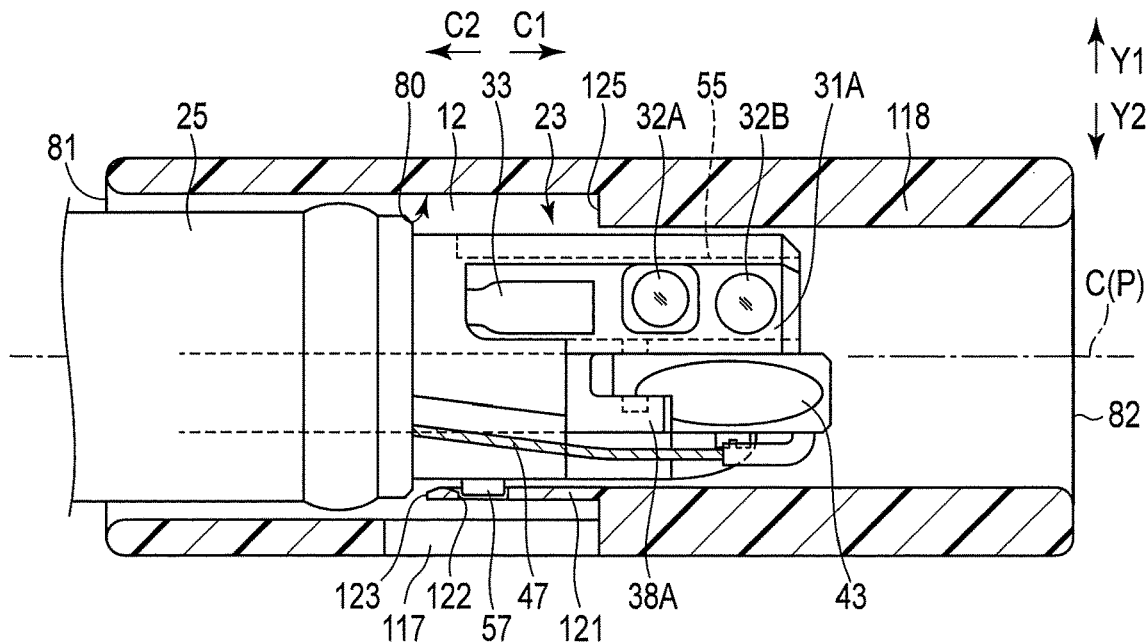
FIG. 18B is a cross-sectional diagram schematically showing a state in which the washing tool main body is attached to a distal framing section of the fifth modification, as viewed in a cross section substantially perpendicular to the first intersecting direction.

In a fifth modification shown in FIGS. 18A and 18B, the washing tool main body 10 is provided with an opening window 117 penetrating from the outer peripheral surface to the storage portion 12. The opening window 117 is located on the insertion opening 81 side with respect to the inflow ports 85A and 85B. Also, the opening window 117 is located at a position that is approximately 90° away from the inflow ports 85A and 85B around the central axis P. In the present modification, a protruding portion (protrusion) 118 protruding inwardly is provided on the inner peripheral surface 80 of the washing tool main body 10. The protruding portion 118 is formed over the entire circumference around the central axis P. The protruding portion 118 also extends from the opening window 82 toward the insertion opening 81 side. Since the protruding portion 118 protrudes inwardly, a step surface 125 is formed at an end of the protruding portion 118 on the insertion opening 81 side in the direction along the central axis P. The step surface 125 is formed over the entire circumference around the central axis P. The inflow ports 85A and 85B are provided on the protruding portion 118. Therefore, the step surface 125 (end of the protruding portion 118 on the insertion opening 81 side) is located on the insertion opening 81 side (arrow P1 side) with respect to the inflow port 85A in the direction along the central axis P. The opening window 117 also extends from the step surface 125 toward the insertion opening 81 side.

In the present modification, an extension piece 121 extends from the step surface 125 toward the insertion opening 81 side in the storage portion 12. The extension piece 121 protrudes from the step surface 125 toward the insertion opening 81 side. The extension piece 121 is located at approximately the same angle position as the opening window 117 around the central axis P. However, the extension piece 121 is located away from the opening window 117 toward the inner periphery side. The extension piece 121 is provided with a lock hole 122 as a tool engagement portion (tool engagement) that penetrates through the extension piece 121. The extension piece 121 also includes an end face 123 that forms an end (protruding end) of the extension piece 121 on the insertion opening 81 side. The lock hole 122 is located between the end face 123 and the step surface 125 in the direction along the central axis P. The lock hole 122 and the end face 123 are located between the edge of the opening window 117 on the insertion opening 81 side and the step surface 125 (edge of the opening window 117 on the opening window 82 side) in the direction along the central axis P. FIG. 18A shows the washing tool main body 10 viewed from the side where the opening window 117 is located with respect to the central axis P. FIG. 18B shows a state in which the washing tool main body 10 is attached to the distal framing section 23, as viewed in a cross section substantially perpendicular to the first intersecting direction.

In the present modification as well, when attaching the washing tool main body 10 to the distal framing section 23, the distal framing section 23 is inserted into the storage portion 12 of the washing tool main body 10 from the insertion opening 81. At this time, the distal framing section 23 is moved toward the opening window 82 side in a state where the lock pin 57 as an endoscope engagement portion (endoscope engagement) is at approximately the same angle position around the longitudinal axis C as the lock hole 122 as a tool engagement portion (tool engagement). Namely, the distal framing section 23 is moved toward the opening window 82 side with the opening window 117 and the lock hole 122 located on the side (arrow Y2 side) where the lock pin 57 is located with respect to the longitudinal axis C, in the second intersecting direction. Then, the lock hole (tool engagement portion) 122 of the washing tool main body 10 is engaged with the lock pin (endoscope engagement portion) 57 of the distal framing section 23. The engagement of the lock hole 122 with the lock pin 57 restricts the movement of the washing tool main body 10 and the insertion section 20 (distal framing section 23) with respect to each other around the longitudinal axis C (central axis P). Therefore, the lock hole 122 as a tool engagement portion positions the washing tool main body 10 with respect to the distal framing section 23 around the longitudinal axis C, so that the lock hole 122 is at approximately the same angle position as the lock pin 57 as an endoscope engagement portion. In the present modification as well, with the washing tool main body 10 positioned with respect to the distal framing section 23 around the longitudinal axis C, the first surface 51 of the swing table 43 faces the side (arrow X1 side) where the inflow ports 85A and 85B are located with respect to the longitudinal axis C in the first intersecting direction, and the second surface 52 faces the side (arrow X2 side) opposite to the side where the inflow ports 85A and 85B are located with respect to the longitudinal axis C in the first intersecting direction.

In the present modification, the lock hole 122 engages with the lock pin 57, thereby restricting the movement of the distal framing section 23 toward the opening window 82 side (distal side). Namely, the lock hole 122 positions the washing tool main body 10 with respect to the distal framing section 23 in the direction along the longitudinal axis C (central axis P). Therefore, in the present modification, the lock hole 122 engages with the lock pin 57, whereby the distal framing section 23 is located at the predetermined position in the storage portion 12 where a fluid such as a washing liquid is supplied. Namely, in the present modification, the lock hole 122 functions as a position adjuster, and defines the position of the distal framing section 23 inside the washing tool main body 10, so that the distal framing section 23 is located at the predetermined position where a fluid is supplied.

In the present modification, the lock hole 122 as a position adjuster engages with the lock pin 57, thereby positioning the washing tool main body 10 with respect to the distal framing section 23 in the direction around the longitudinal axis C and the direction along the longitudinal axis C. Then, the lock pin 57 engages with the lock hole (cover engagement portion) 75 of the cover 5 when attaching the cover 5 to the distal framing section 23. Therefore, with the structure necessary for attaching the cover 5 to the distal framing section 23, the position of the distal framing section 23 inside the washing tool main body 10 is defined, so that the distal framing section 23 is located at the predetermined position.

In the present modification, the lock hole 122 engages with the lock pin 57, thereby generating a clicking sound. Therefore, the operator can determine, based on the presence or absence of the click feeling, whether or not the distal framing section 23 has moved to the aforementioned predetermined position in the storage portion 12.

In the present modification, because of the above-described structure, the operator can release the engagement of the lock hole 122 with the lock pin 57 through the opening window 117 in the state where the distal framing section 23 is located at the aforementioned predetermined position in the storage portion 12. As such, the engagement of the lock hole 122 with the lock pin 57 is easily released. Accordingly, the washing tool main body 10 is easily detached from the distal framing section 23.

Also, in the present modification, when the distal framing section 23 is inserted into the storage portion 12 from the insertion opening 81 with the cover 5 attached to the distal framing section 23, the distal portion of the cover 5 abuts on the end face 123 of the extension piece 121 and interferes with the extension piece 121. As a result, the movement of the distal framing section 23 and the cover 5 from the end face 123 toward the opening window 82 side (distal side) is restricted. Since the cover 5 and the distal framing section 23 cannot move from the end face 123 of the extension piece 121 toward the opening window 82 side in the storage portion 12, the distal framing section 23 with the cover 5 attached thereto cannot move to the aforementioned predetermined position in the storage portion 12. Namely, in the present modification, the extension piece 121 functions as a regulator, and the extension piece 121 interferes with the cover 5, thereby restricting the movement of the distal framing section 23 with the cover 5 attached thereto to the predetermined position.

Figure 19A:
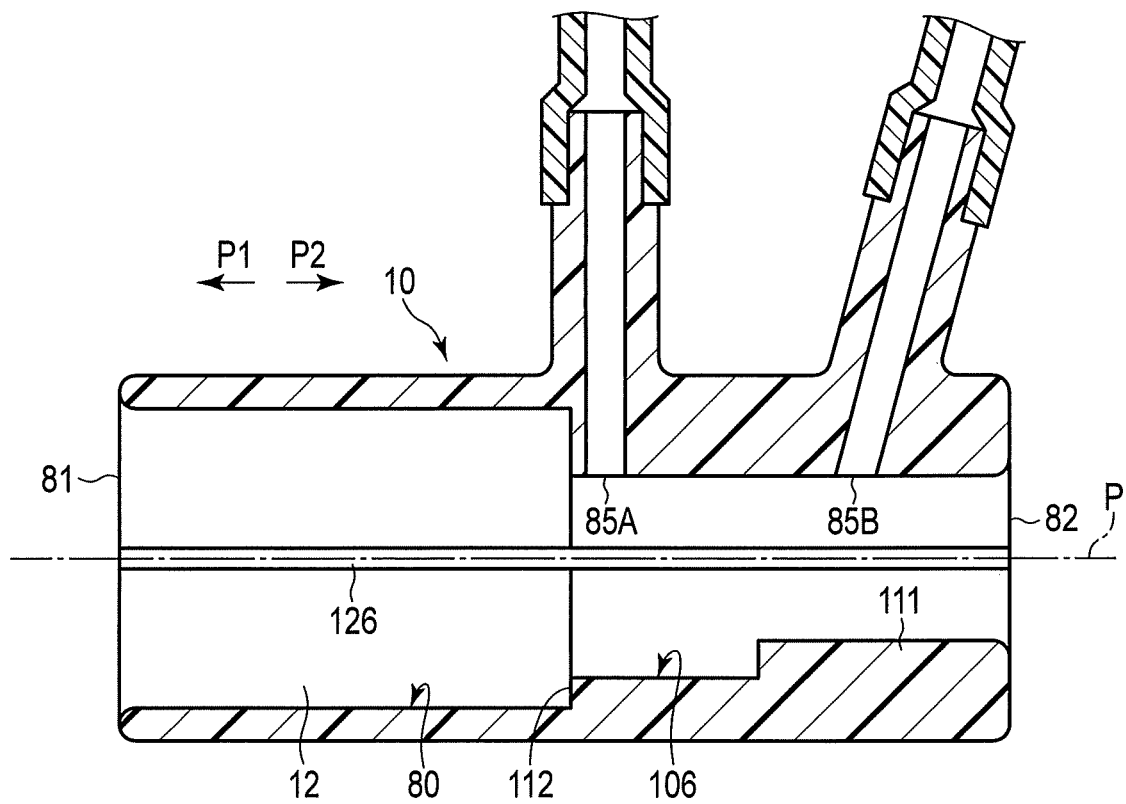
FIG. 19A is a cross-sectional diagram schematically showing a washing tool main body of a sixth modification, as viewed in a cross section substantially parallel with the central axis.
Figure 19B:
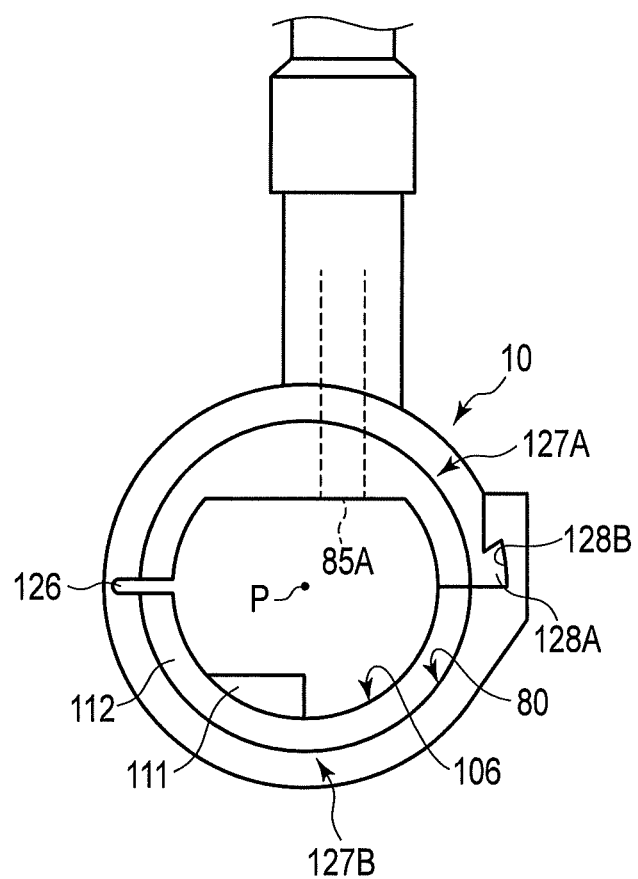
FIG. 19B is a schematic diagram of a state in which turning pieces are closed in the washing tool main body of the sixth modification, as viewed from the insertion opening side.
Figure 20:
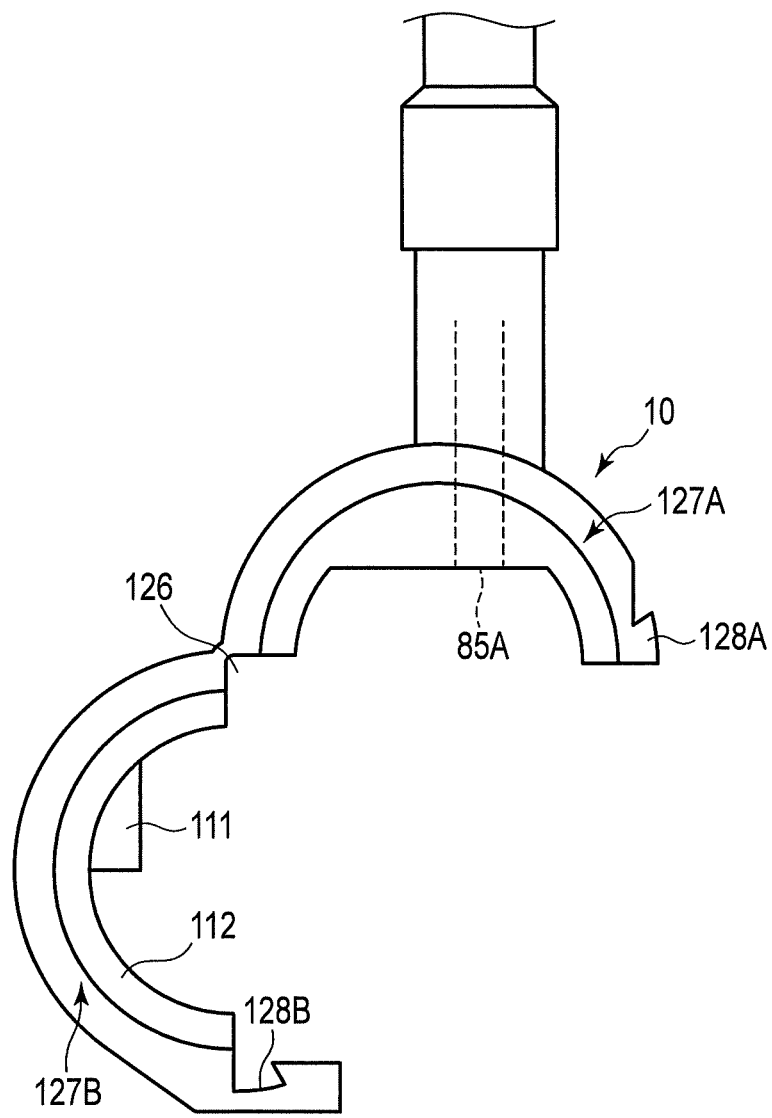
FIG. 20 is a schematic diagram of a state in which the turning pieces are opened in the washing tool main body of the sixth modification, as viewed from the insertion opening side.

In a sixth modification shown in FIGS. 19A to 20, a groove 126 recessed toward the outer periphery side is formed on the inner peripheral surface 80 of the washing tool main body 10, in addition to the structure similar to that of the third modification. The groove 126 extends continuously from the insertion opening 81 to the opening window 82 along the rotation axis P. Also, the groove 126 is located at a position that is approximately 90° away from the inflow ports 85A and 85B around the central axis P. In the present modification, the washing tool main body 10 includes turning pieces 127A and 127B. The turning pieces 127A and 127B are turnable with respect to each other about the rotation axis substantially parallel to the central axis P and passing through the groove 126. As the turning pieces 127A and 127B turn about the rotation axis, the turning pieces 127A and 127B open or close. Therefore, in the present modification, the washing tool main body 10 has a hinge structure in which the turning pieces 127A and 127B can be opened and closed relative to each other.

The turning piece 127A is provided with an engagement protrusion 128A, and the turning piece 127B is provided with an engagement depressed portion (engagement recess) 128B. The turning pieces 127A and 127B are closed and the engagement protrusion 128A is engaged with the engagement depressed portion 128B, whereby the washing tool main body 10 has a tubular shape so that the storage portion 12 is formed therein. With the engagement protrusion 128A engaged with the engagement depressed portion 128B, the turning of the turning pieces 127A and 127B about the above-described rotation axis passing through the groove 126 is restricted. The engagement protrusion 128A and the engagement depressed portion 128B are located at a position that is approximately 90° away from the inflow ports 85A and 85B and at a position that is approximately 180° away from the groove 126 around the central axis P. FIG. 19A shows a cross section that is substantially parallel to the central axis P of the washing tool main body 10. FIG. 19B and FIG. 20 show the washing tool main body 10 viewed from the insertion opening 81 side. FIG. 19B shows a state in which the turning pieces 127A and 127B are closed and the engagement protrusion 128A is engaged with the engagement depressed portion 128B. FIG. 20 shows a state in which the turning pieces 127A and 127B are opened.

In the present modification, the distal framing section 23 can be inserted into the storage portion 12 from the insertion opening 81, and opening the turning pieces 127A and 127B also allows the distal framing section 23 to be inserted into the storage portion 12 from the direction intersecting the central axis P. As in the third modification, the restriction inner peripheral surface 106 and the protruding portion 111 function as position adjusters, and define the position of the distal framing section 23 inside the washing tool main body 10, so that the distal framing section 23 is located at the predetermined position where a fluid is supplied. With the distal framing section 23 located at the aforementioned predetermined position, the turning pieces 127A and 127B are closed and the engagement protrusion 128A is engaged with the engagement depressed portion 128B. Also, with the turning pieces 127A and 127B closed and the engagement protrusion 128A engaged with the engagement depressed portion 128B, the distal framing section 23 is washed as described above.

In the present modification, as in the third modification, when the distal framing section 23 is inserted into the storage portion 12 from the insertion opening 81 with the cover 5 attached to the distal framing section 23, the step surface 112 interferes with the cover 5, thereby restricting the movement of the distal framing section 23 with the cover 5 attached thereto to the predetermined position. In the present modification, when the distal framing section 23 with the cover 5 attached thereto is inserted into the storage portion 12 from the direction intersecting the central axis P with the turning pieces 127A and 127B opened, the closing motion of the turning pieces 127A and 127B is restricted. Therefore, the turning pieces 127A and 127B are not closed, so that the engagement protrusion 128A cannot be engaged with the engagement depressed portion 128B. As a result, the washing tool main body 10 does not have a tubular shape, and the movement of the distal framing section 23 with the cover 5 attached thereto to the predetermined position is restricted. Therefore, in the present modification, the turning pieces 127A and 127B also function as regulators, and the turning pieces 127A and 127B interfere with the cover 5, thereby restricting the movement of the distal framing section 23 with the cover 5 attached thereto to the predetermined position.

As a further modification of the sixth modification, a structure may be adopted in which the distal framing section 23 can be inserted into the storage portion 12 only from the direction intersecting the central axis P with the turning pieces 127A and 127B opened. In this structure, even when the turning pieces 127A and 127B are closed, the distal framing section 23 cannot be inserted into the storage portion 12 from the insertion opening 81 in the direction along the central axis P. Also, the structure of the sixth modification in which the turning pieces 127A and 127B open and close may be combined with the embodiments, other than the third modification, such as the first embodiment.

In a seventh modification shown in FIG. 21, the supply section (supplier) 11 of the washing tool 2 includes pumps 135A and 135B in place of the syringes 18A and 18B. In the present modification, the pump 135A is driven, so that a liquid such as a washing liquid is supplied to the inflow port 85A through the supply tube 15A. Also, the pump 135B is driven, so that a liquid such as a washing liquid is supplied to the inflow port 85B through the supply tube 15B.

In one modification (not shown in the drawings), only one syringe (18A) or only one pump (135A) may be provided to the supply section 11. In this case as well, the two inflow ports 85A and 85B are provided to the washing tool main body 10, as in the above-described embodiment and the like. In this case, a supply path branches into two parts at the downstream side of the syringe (18A) or the downstream side of the pump (135A). One of the branched parts of the supply path communicates with the inflow port 85A, and the other branched part of the supply path communicates with the inflow port 85B.

Also, in one modification (not shown in the drawings), three or more inflow ports (e.g., inflow ports 85A to 85C) may be provided to the washing tool main body 10. In this case, as in the above-described embodiment and the like, it is preferable that, with the distal framing section 23 located at the aforementioned predetermined position in the storage portion 12, at least one of the plurality of inflow ports (e.g., inflow port 85A) supplies a fluid to the first surface 51 of the swing table 43, and at least one of the other inflow ports (e.g., inflow port 85B) supplies a fluid to the second surface 52 of the swing table 43.

Also, in one modification, the turning pieces 127A and 127B are opened and closed as described in the sixth modification, and after the supply path branches into multiple parts, each of the branched parts of the supply path communicates with a corresponding one of the plurality of inflow ports (e.g., inflow ports 85A and 85B). In the structure of the present modification, the plurality of inflow ports (85A and 85B) are preferably not provided on both sides with the groove 126 therebetween. Namely, all the inflow ports (85A and 85B) are preferably formed in only one of the turning pieces 127A and 127B. As a result, the operation of engaging the engagement protrusion 125A and the engagement depressed portion 128B is less likely to be inhibited by the supply path to the inflow ports (85A and 85B).

In the above-described embodiment and the like, the washing tool main body 10 is formed in a substantially cylindrical shape; however, if the washing tool main body 10 has a tubular shape so that the storage portion 12 is formed therein, the washing tool main body 10 may be formed in a substantially polygonal tubular shape, such as a substantially quadrangular tubular shape or a substantially triangular tubular shape. Also, in one modification, many opening windows (82) may be formed on the outer surface of the washing tool main body 10.

Figure 22A:
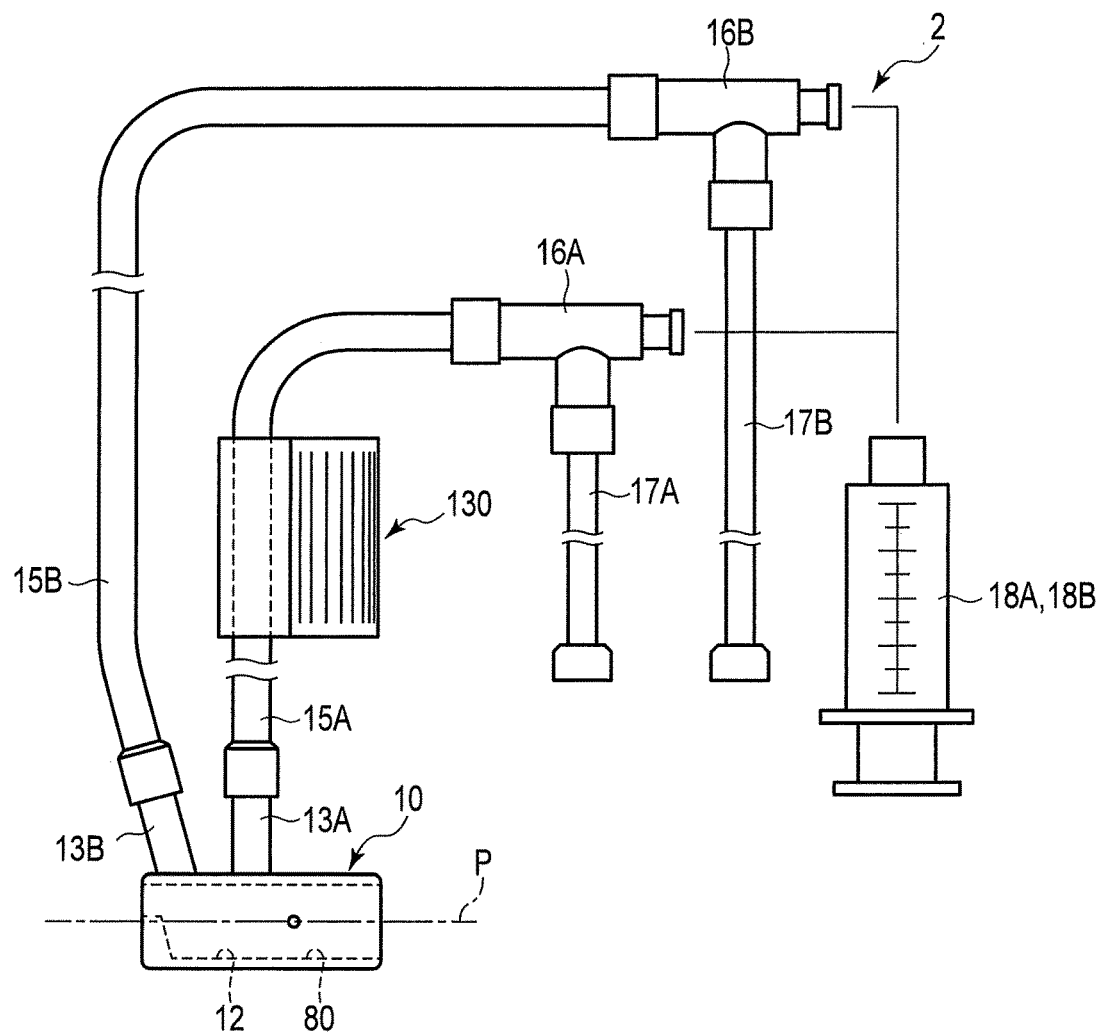
FIG. 22A is a schematic diagram of a washing tool of an eighth modification.
Figure 22B:
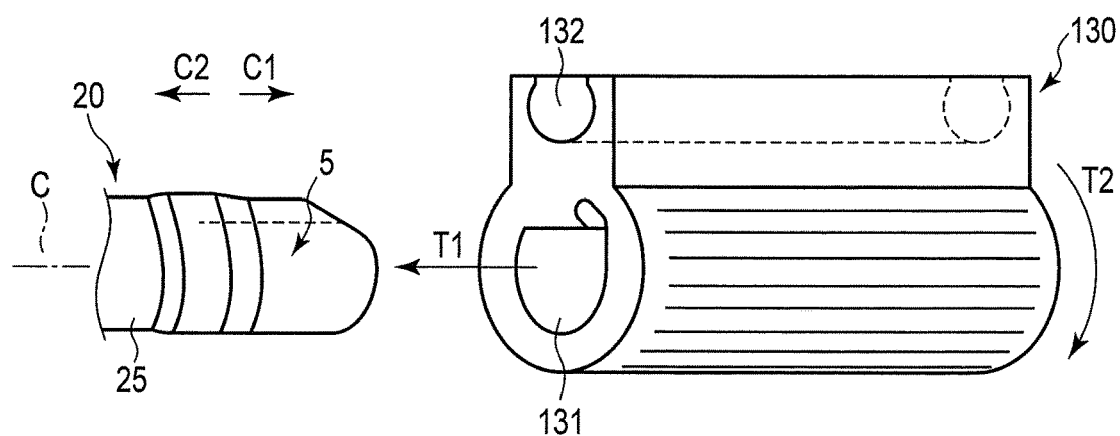
FIG. 22B is a schematic diagram illustrating a method of detaching the cover from the distal framing section by using a jig provided in the washing tool of the eighth modification.

In an eighth modification shown in FIGS. 22A and 22B, a jig 130 is detachably attached to the supply tube 15A in the supply section 11 of the washing tool 2. In this modification, the jig 130 is, for example, the aforementioned jig used when detaching the cover 5 from the distal framing section 23. Examples of a material forming the jig 130 include, but are not limited to, polycarbonate, a modified PPE resin, polysulfone containing glass, polyphenylsulfone, and stainless steel. The jig 130 may be attached to the supply tube 15B, for example. It is sufficient as long as the jig 130 is attached to any part of the washing tool 2.

A cavity 131 into which the distal framing section 23 with the cover 5 attached thereto is inserted is formed in the jig 130. Also, an engagement groove 132, which engages with the supply tube 15A (or 15B), is formed in the jig 130. The engagement groove 132 engages with the supply tube 15A, whereby the jig 130 is attached to the supply tube 15A.

When detaching the cover 5 from the distal framing section 23, the distal framing section 23 with the cover 5 attached thereto is inserted into the cavity 131 of the jig 130 from the distal side (arrow T1 in FIG. 22B). Then, the jig 130 is turned with respect to the distal framing section 23 and the cover 5 to one side around the longitudinal axis C (central axis of the jig 130). As a result, the fragile portion 78 of the cover 5 is broken as described above, so that the slits 77A and 77B are continuous with each other. Then, the engagement of the lock pin 57 with the lock hole 75 is released. With the engagement of the lock pin 57 with the lock hole 75 released, the distal framing section 23 is pulled out of the cavity 131, so that the guide protrusion 74 moves toward the distal side in the guide groove 55. As a result, the cover 5 moves toward the distal side relative to the distal framing section 23, so that the cover 5 is detached from the distal framing section 23.

In the present modification, since the jig 130 is attached to the washing tool 2, it is possible to quickly and easily detach the cover 5 from the distal framing section 23 and attach the washing tool main body 10 to the distal framing section 23 from which the cover 5 has been detached. For example, the trouble of looking for the jig 130 used for detaching the cover 5 from the distal framing section 23 is avoided.

In the above-described embodiment and the like, the endoscope 3 is a side-viewing or oblique-viewing endoscope in which the direction intersecting the longitudinal axis C of the insertion section 20 is the observing direction of the imaging element. However, the endoscope 3 is not limited thereto. In one modification, the above-described structure may be applied to a direct-viewing endoscope in which the direction along the longitudinal axis C of the insertion section 20 is the observing direction of the imaging sensor.

In the above-described embodiment and the like, the washing tool main body (10) of the washing tool (2) is attached to the distal framing section (23) of the insertion section (20) of the endoscope (3) in place of the cover (5), and with the washing tool main body (10) attached to the distal framing section (23), the distal framing section (23) is housed inside the washing tool main body (10). Also, the washing tool (2) is provided with the supply section (11) configured to supply a fluid into the washing tool main body (10). When attaching the washing tool main body (10) to the distal framing section (23), the position of the distal framing section (23) inside the washing tool main body (10) is defined by the position adjusters (87; 88A, 88B, 100; 106; 111; 122), so that the distal framing section 23 is located at the predetermined position where a fluid is supplied. When the distal framing section (23) with the cover (5) attached thereto is inserted into the washing tool main body (10), the regulators (87, 88A, 88B; 88A, 88B, 100; 112; 121; 127A, 127B) interfere with the cover (5) and restrict the movement of the distal framing section (23) with the cover (5) attached thereto to the predetermined position.

The structure of the distal framing section 23 and the structure of the cover 5 are not limited to the above-described embodiment and the like as long as they satisfy such a structure. Also, the structure of attaching the cover 5 to the distal framing section 23 is not limited to the above-described embodiment and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an endoscope comprising an insertion section, the insertion section including a distal framing section at a distal end of the insertion section;
   a cover configured to be detachably attached to the distal framing section;
   a washing tool main body having a central axis, the washing tool main body having a storage cavity formed inside the washing tool main body, the storage cavity having a first opening at a first end in a direction along the central axis, the distal framing section being configured to be inserted into the storage cavity from the first end and configured to move in the storage cavity from the first end to a predetermined position along the central axis, the washing tool main body comprising a first turning piece and a second turning piece, the second turning piece being openable and closable relative to the first turning piece about a hinge having an axis of rotation parallel with an insertion direction of the distal framing section into the storage cavity, the second tuning piece comprising an engagement part configured to engage with the first turning piece, the washing tool main body being formed into a tubular shape having the storage cavity when the second turning piece is engaged with the first turning piece;
   an inflow port formed in the washing tool main body, the inflow port being in fluid communication with the storage cavity of the washing tool main body to supply washing fluid to the distal framing section positioned in the predetermined position; and
   a regulator provided in the storage cavity, the regulator being located between the first opening and the inflow port in the direction along the central axis, the regulator forming a guide and a stopper, the guide being configured to guide the distal framing section without the cover from the first end to the predetermined position in the storage cavity, the stopper being configured to restrict movement of the distal framing section with the cover to the predetermined position in the storage cavity,
   wherein the distal framing section includes a guide groove,
   the stopper comprises a pin projecting from an inner surface of the storage cavity toward the central axis, the pin being configured to engage with the guide groove to allow the distal framing section without the cover to be moved into the storage cavity until the distal framing section reaches the predetermined position;
   the pin being configured to restrict movement of the distal framing section with the cover into the storage cavity; and
   the guide comprises one or more rails projecting from the inner surface of the storage cavity toward the central axis, the one or more rails extending along the central axis.

2. The endoscope system according to claim 1, wherein the first and second turning pieces open relative to each other such that the distal framing section is inserted into the storage cavity from a direction intersecting the central axis.

3. An endoscope system comprising:
   an endoscope comprising an insertion section, the insertion section including a distal framing section at a distal end of the insertion section;
   a cover configured to be detachably attached to the distal framing section;
   a washing tool main body having a central axis, the washing tool main body having a storage cavity formed inside the washing tool main body, the storage cavity having a first opening at a first end in a direction along the central axis, the distal framing section being configured to be inserted into the storage cavity from the first end and configured to move in the storage cavity from the first end to a predetermined position along the central axis, the washing tool main body comprising a first turning piece and a second turning piece, the second turning piece being openable and closable relative to the first turning piece about the hinge having an axis of rotation parallel with an insertion direction of the distal framing section into the storage cavity, the second tuning piece comprising an engagement part configured to engage with the first turning piece, the washing tool main body being formed into a tubular shape having the storage cavity when the second turning piece is engaged with the first turning piece;
   an inflow port formed in the washing tool main body, the inflow port being in fluid communication with the storage cavity of the washing tool main body to supply washing fluid to the distal framing section positioned in the predetermined position;
   a regulator provided in the storage cavity, the regulator being located between the first opening and the inflow port in the direction along the central axis, the regulator forming a guide and a stopper, the guide being configured to guide the distal framing section without the cover from the first end to the predetermined position in the storage cavity, the stopper being configured to restrict movement of the distal framing section with the cover to the predetermined position in the storage cavity;
   a protrusion protruding from an inner surface of the storage cavity, the protrusion being positioned adjacent to a second end on the inner surface of the storage cavity, the second end being an opposite end of the first end in the direction along the central axis, the protrusion comprising a wall surface which is inclined relative to the central axis of the washing tool main body; and
   an other inflow port in fluid communication with the storage cavity, the other inflow port being disposed further from the first end than the inflow port in the direction along the central axis of the washing tool main body, a port axis of the other inflow port being substantially parallel with the wall surface of the protrusion, the port axis of the other inflow port intersecting with the central axis of the washing tool main body at an acute angle such that the fluid is directed toward the first end of the washing tool main body,
   wherein in a state where the distal framing section of the endoscope is inserted into the storage cavity of the washing tool main body, an extension line of the port axis of the other inflow port passes between the distal framing section and the protrusion, and a port axis of the inflow port perpendicularly intersects with the central axis of the washing tool main body.

4. The endoscope system according to claim 3, wherein the storage cavity having the first opening at the first end of the washing tool main body in which the distal framing section enters the storage cavity and a second opening at an opposite end of the washing tool main body in the direction along the central axis, the second opening being at least partially defined by a top surface of the protrusion, the second opening being smaller than the first opening.

* * * * *